(12) United States Patent
Georges et al.

(10) Patent No.: US 10,610,566 B1
(45) Date of Patent: Apr. 7, 2020

(54) **INDUCING CNS NEURITE OUTGROWTH WITH *MOMORDICA COCHINCHINENSIS* EXTRACT**

(71) Applicant: Florida A&M University, Tallahassee, FL (US)

(72) Inventors: Beatrice Georges, Tallahassee, FL (US); Elizabeth Mazzio, Quincy, FL (US); Karam Soliman, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 16/144,208

(22) Filed: Sep. 27, 2018

Related U.S. Application Data

(62) Division of application No. 15/419,329, filed on Jan. 30, 2017, now abandoned.

(60) Provisional application No. 62/289,735, filed on Feb. 1, 2016.

(51) Int. Cl.
*A61K 38/16* (2006.01)
*A23L 33/105* (2016.01)
*A23L 33/00* (2016.01)
*A61K 36/42* (2006.01)

(52) U.S. Cl.
CPC .......... *A61K 38/168* (2013.01); *A23L 33/105* (2016.08); *A23L 33/40* (2016.08); *A61K 36/42* (2013.01); *A23V 2002/00* (2013.01)

(58) Field of Classification Search
CPC .............................. A61K 38/56; A61K 38/168
See application file for complete search history.

(56) References Cited

PUBLICATIONS

Jackowski, British J. Neurosurgery 9: 303-317 (Year: 1995).*
Levi-Montalcini, R. et al., In vitro and in vivo effects of a nerve growth-stimulating agent isolated from snake venom. Proc Natl Acad Sci USA. 1956;42:695-699.
Esmaeili, A. et al., Messenger RNA expression patterns of neurotrophins during transdifferentiation of stem cells from human-exfoliated deciduous teeth into neural-like cells. Avicenna J Med Biotechnol. 2014;6:21-26.
Bothwell, M. NGF, BDNF, NT3, and NT4. Handb Exp Pharmacol. 2014;220:3-15.
Kao, T.H. et al., Nerve growth factor promotes expression of novel genes in intervertebral disc cells that regulate tissue degradation. J Neurosurg Spine1-9Spine. 2014;21:653-656.
Backman, C. et al., Systemic administration of a nerve growth factor conjugate reverses age-related cognitive dysfunction and prevents cholinergic neuron atrophy. J Neurosci. 1996;16:5437-5442.
Poduslo, J.F. et al., Permeability at the blood-brain and blood-nerve barriers of the neurotrophic factors: NGF, CNTF, NT-3, BDNF. Brain Res Mol Brain Res. 1996;36:280-286.
Cui, X. et al., Genetic modification of mesenchymal stem cells in spinal cord injury repair strategies. Biosci Trends. 2013;7:202-208.
Kuifiua, Z et al., Aligned SF/P(LLA-CL)-blended nanofibers encapsulating nerve growth factor for peripheral nerve regeneration. J Biomed Mater Res, Part A. 2014;102:2680-2691.
Kuo, Y.C. et al., Protection of SK-N-MC cells against beta-amyloid peptide-induced degeneration using neuron growth factor-loaded liposomes with surface lactoferrin. Biomaterials. 2014;35:5954-5964.
Yu, H. et al., Local delivery of controlled released nerve growth factor promotes sciatic nerve regeneration after crush injury. Neurosci Lett. 2014;566:177-181.
Povarnina, P.Y., Original nerve growth factor mimetic dipeptide GK-2 restores impaired cognitive functions in rat models of Alzheimer's disease. Acta Naturae. 2013;5:84-91.
Zhao, G.Y. et al., Intrathecal lidocaine neurotoxicity: combination with bupivacaine and ropivacaine and effect of nerve growth factor. Life Sci. 2014;112:10-21.
Zhang, H. et al., Nerve growth factor improves functional recovery by inhibiting endoplasmic reticulum stress-induced neuronal apoptosis in rats with spinal cord injury. J Transl Med. 2014;12:130.
Evans, S.M. et al., Development of a high throughput in vitro toxicity screen predictive of high acute in vivo toxic potential. Toxicol In Vitro. 2001;15:579-584.
Dileonardi, A.M. et al., Differential effects of FK506 on structural and functional axonal deficits after diffuse brain injury in the immature rat. J Neuropathol Exp Neurol. 2012;71:959-972.
Cheng, L. et al., Lentiviral-mediated transfer of CDNF promotes nerve regeneration and functional recovery after sciatic nerve injury in adult rats. Biochem Biophys Res Commun. 2013;440:330-335.
Figley, S.A. et al., Delayed administration of a bio-engineered zinc-finger VEGF-A gene therapy is neuroprotective and attenuates allodynia following traumatic spinal cord injury. PLoS One. 2014;9:e96137.
Chen, G. et al., Combined treatment with FK506 and nerve growth factor for spinal cord injury in rats. Exp Ther Med. 2013;6:868-872.
Aletta, J.M. et al., Growth cone configuration and advance: a time-lapse study using video-enhanced differential interference contrast microscopy. J Neurosci. 1988;8:1425-1435.

(Continued)

*Primary Examiner* — Robert C Hayes
(74) *Attorney, Agent, or Firm* — Michele L. Lawson; Smith & Hopen, P.A.

(57) ABSTRACT

Compositions and methods for preventing and treating central nervous system (CNS) diseases and disorders (e.g., Alzheimer's disease, Parkinson's disease, etc.). The composition includes an aqueous extract of the *Momordica cochinchinensis* seed, specifically total plant protein isolate containing *Momordica cochinchinensis* trypsin inhibitor II. The method of preventing/treating the CNS disease includes administering a therapeutically effective amount of the *Momordica cochinchinensis* seed extract to a patient. The seed extract functions as a nerve growth factor mimetic and can penetrate the BBB and initiate CNS neuronal outgrowth/regeneration.

8 Claims, 21 Drawing Sheets
(19 of 21 Drawing Sheet(s) Filed in Color)

(56) References Cited

PUBLICATIONS

Mitchell, D.J. et al., Trk activation of the ERK1/2 kinase pathway stimulates intermediate chain phosphorylation and recruits cytoplasmic dynein to signaling endosomes for retrograde axonal transport. J Neurosci. 2012;32:15495-15510.

Song, E.J. et al., Nerve growth factor-induced neurite outgrowth is potentiated by stabilization of TrkA receptors. BMB Rep. 2011;44:182-186.

Arimura, N. et al., Anterograde transport of TrkB in axons is mediated by direct interaction with Slp1 and Rab27. Dev Cell. 2009;16:675-686.

Pradines, A. et al., Evidence for nerve growth factor-potentiating activities of the nonpeptidic compound SR 57746A in PC12 cells. J Neurochem. 1995;64:1954-1964.

Thauerer, B. et al., LAMTOR2-mediated modulation of NGF/MAPK activation kinetics during differentiation of PC12 cells. PLoS One. 2014;9:e95863.

Chen, J.H. et al., Cytotoxic effects of acrylamide in nerve growth factor or fibroblast growth factor 1-induced neurite outgrowth in PC12 cells. Arch Toxicol. 2014;88:769-780.

Terada, K. et al., Inhibition of nerve growth factor-induced neurite outgrowth from PC12 cells by dexamethasone: signaling pathways through the glucocorticoid receptor and phosphorylated Akt and ERK1/2. PLoS One. 2014;9:e93223.

Nishina, A. et al., Neurite outgrowth of PC12 cells by 4'-O-beta-D-glucopyranosyl-3',4-dimethoxychalcone from Brassica rapa L. 'hidabeni' was enhanced by pretreatment with p38MAPK inhibitor. Neurochem Res. 2013;38:2397-2407.

Chijiwa, T. et al., Inhibition of forskolin-induced neurite outgrowth and protein phosphorylation by a newly synthesized selective inhibitor of cyclic AMP-dependent protein kinase, N-[2-(p-bromocinnamylamino)ethyl]-5-soquinolinesulfonamide (H-89), of PC12D pheochromocytoma cells. J Biol Chem. 1990;265:5267-5272.

Emery, A.C. et al., Separate cyclic AMP sensors for neuritogenesis, growth arrest, and survival of neuroendocrine cells. J Biol Chem. 2014;289:10126-10139.

Wang, L. et al., Rab22 controls NGF signaling and neurite outgrowth in PC12 cells. Mol Biol Cell. 2011;22:3853-3860.

Suo, D. et al., Coronin-1 is a neurotrophin endosomal effector that is required for developmental competition for survival. Nat Neurosci. 2014;17:36-45.

Fujita, A. et al., GTP hydrolysis of TC10 promotes neurite outgrowth through exocytic fusion of Rab11-and L1-containing vesicles by releasing exocyst component Exo70. PLoS One. 2013;8:e79689.

Pommereit, D. et al., An NGF-induced Exo70-TC10 complex locally antagonises Cdc42-mediated activation of N-WASP to modulate neurite outgrowth. J Cell Sci. 2007;120:2694-2705.

Spillane, M. et al., Nerve growth factor-induced formation of axonal filopodia and collateral branches involves the intra-axonal synthesis of regulators of the actin-nucleating Arp2/3 complex. J Neurosci. 2012;32:17671-17689.

Mingorance-Le Meur, A. et al., Varicones and growth cones: two neurite terminals in PC12 cells. PLoS One. 2009;4:e4334.

Aoki, H. et al., Carotenoid pigments in GAC fruit (*Momordica cochinchinensis* SPRENG) Biosci Biotechnol Biochem. 2002;66:2479-2482.

Park, S. et al., Cyclotide structure-activity relationships: qualitative and quantitative approaches linking cytotoxic and anthelmintic activity to the clustering of physicochemical forces. PLoS One. 2014;9:e91430.

Heitz, A. et al., Solution structure of the squash trypsin inhibitor MCoTI-II. A new family for cyclic knottins. Biochemistry. 2001;40:7973-7983.

Kliemannel, M. et al., Examination of the slow unfolding of pro-nerve growth factor argues against a loop threading mechanism for nerve growth factor. Biochemistry. 2006;45:3517-3524.

\* cited by examiner

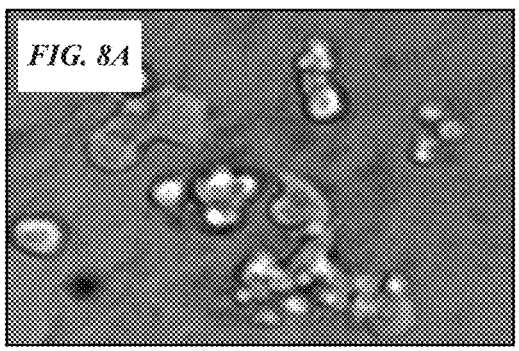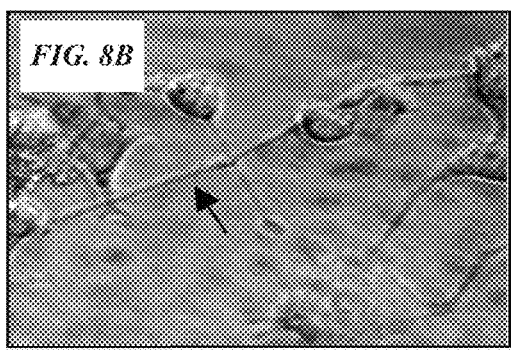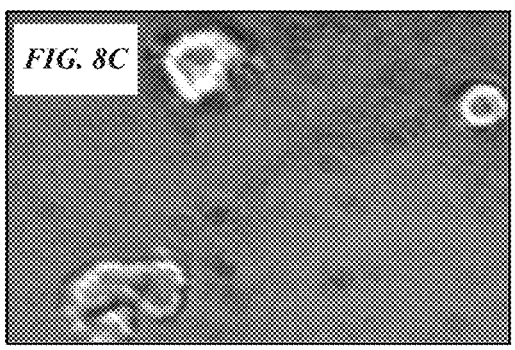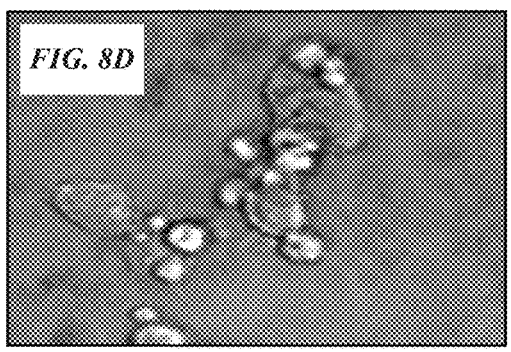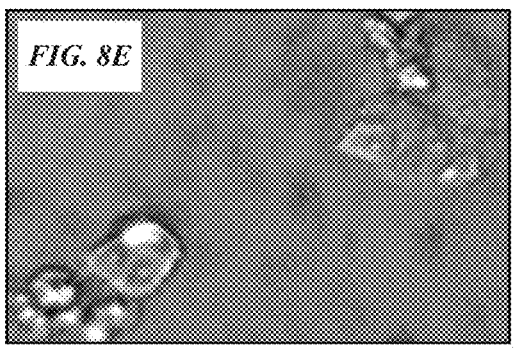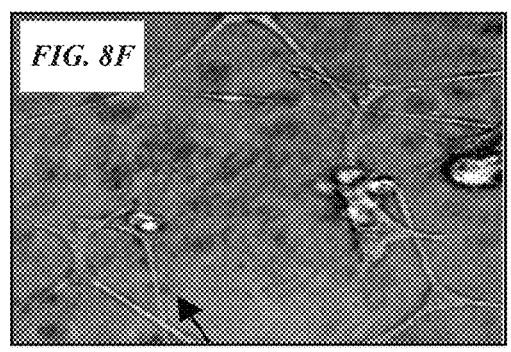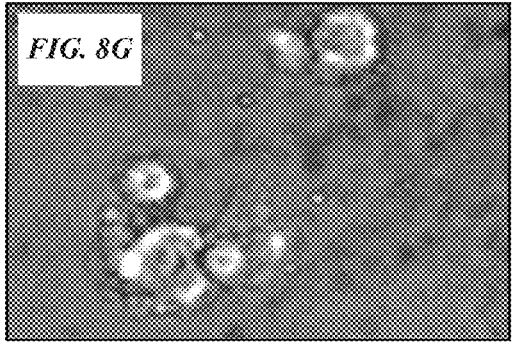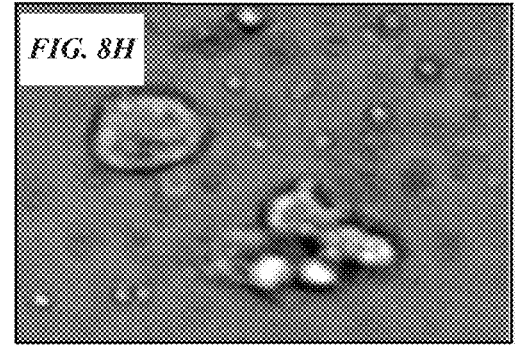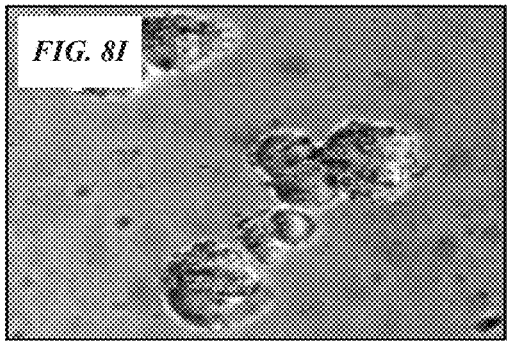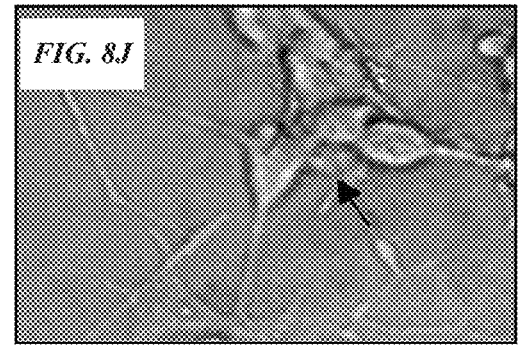

INDUCING CNS NEURITE OUTGROWTH WITH *MOMORDICA COCHINCHINENSIS* EXTRACT

CROSS-REFERENCE TO RELATED APPLICATIONS

This application is a divisional of and claims priority to U.S. Nonprovisional application Ser. No. 15/419,329, entitled "Neurotrophic Supportive Nutraceutical for Treatment of Degenerative CNS Disease," filed Jan. 30, 2017 by the same inventors, which is a nonprovisional application claiming priority to U.S. Provisional Patent Application No. 62/289,735, entitled "Neurotrophic Supportive Nutraceutical for Treatment of Degenerative CNS Diseases", filed Feb. 1, 2016 by the same inventors, the entirety of each are incorporated herein by reference.

FEDERALLY SPONSORED RESEARCH OR DEVELOPMENT

This invention was made with Government support under Grant Nos. G12 MD007582 and P20 MD006738 awarded by the National Institutes of Health. The government has certain rights in the invention.

BACKGROUND

1. Field of the Invention

This invention relates, generally, to treatment and/or prevention of diseases affecting/injuring the central nervous system (CNS). More specifically, it relates to neurotrophic supportive nutraceuticals that aid in treatment and/or prevention of CNS diseases, for example Alzheimer's disease and Parkinson's disease.

2. Brief Description of the Prior Art

Post-mitotic central nervous system (CNS) neurons have limited capacity for regeneration, creating a challenge in the development of effective therapeutics for spinal cord injury or neurodegenerative diseases. Furthermore, therapeutic use of human neurotrophic agents such as nerve growth factor (NGF) are limited due to hampered transport across the blood brain barrier (BBB) and substantial peripheral side effects (e.g., neuro-inflammatory pain/tissue degeneration etc.). Moreover, NGF in therapeutically active forms is thus far limited to invasive [Yosipovitch G. Dry skin and impairment of barrier function associated with itch—new insights. Int J Cosmet Sci. 2004; 26:1-7] NGF-loaded microspheres [Teresiak-Mikolajczak E, Czarnecka-Operacz M, Jenerowicz D, Silny W. Neurogenic markers of the inflammatory process in atopic dermatitis: relation to the severity and pruritus. Postepy Dermatologii i Alergologii. 2013; 30:286-292] or other types of basal forebrain implants [McMahon S B, Cafferty W B, Marchand F. Immune and glial cell factors as pain mediators and modulators. Exp Neurol. 2005; 192:444-462; Bannwarth B, Kostine M. Targeting nerve growth factor (NGF) for pain management: what does the future hold for NGF antagonists? Drugs. 2014; 74:619-626] requiring stereotactic injection techniques [Kim J S, Kang J Y, Ha J H, Lee H Y, Kim S J, Kim S C, Ahn J H, Kwon S S, Kim Y K, Lee S Y. Expression of nerve growth factor and matrix metallopeptidase-9/tissue inhibitor of metalloproteinase-1 in asthmatic patients. J Asthma: Off J Assoc Care Asthma. 2013; 50:712-717].

The neuro-protective/trophic properties of NGF are well established [Kuihua, Z., Chunyang, W., Cunyi, F., Xiumei, M., 2014. Aligned SF/P(LLA-CL)-blended nanofibers encapsulating nerve growth factor for peripheral nerve regeneration. Journal of biomedical materials research. Part A 102, 2680-2691; Zhang, H., Wu, F., Kong, X., Yang, J., Chen, H., Deng, L., Cheng, Y., Ye, L., Zhu, S., Zhang, X., Wang, Z., Shi, H., Fu, X., Li, X., Xu, H., Lin, L., Xiao, J., 2014. Nerve growth factor improves functional recovery by inhibiting endoplasmic reticulum stress-induced neuronal apoptosis in rats with spinal cord injury. Journal of translational medicine 12, 130; Zhao, G. Y., Ding, X. D., Guo, Y., Chen, W. M., 2014. Intrathecal lidocaine neurotoxicity: Combination with bupivacaine and ropivacaine and effect of nerve growth factor. Life Sci. 2014; 112:10-21].

NGF signaling involves phosphorylation of tropomyosin-related kinase receptor (Trk) (A-C), subsequent internalization of the TrKA receptor complex [Abu El-Asrar, A. M., Mohammad, G., De Hertogh, G., Nawaz, M. I., Van Den Eynde, K., Siddiquei, M. M., Struyf, S., Opdenakker, G., Geboes, K., 2013. Neurotrophins and neurotrophin receptors in proliferative diabetic retinopathy. PloS one 8, e65472; Arimura, N., Kimura, T., Nakamuta, S., Taya, S., Funahashi, Y., Hattori, A., Shimada, A., Menager, C., Kawabata, S., Fujii, K., Iwamatsu, A., Segal, R. A., Fukuda, M., Kaibuchi, K., 2009. Anterograde transport of TrkB in axons is mediated by direct interaction with Slp1 and Rab27. Developmental c ell 16, 675-686; Mitchell, D. J., Blasier, K. R., Jeffery, E. D., Ross, M. W., Pullikuth, A. K., Suo, D., Park, J., Smiley, W. R., Lo, K. W., Shabanowitz, J., Deppmann, C. D., Trinidad, J. C., Hunt, D. F., Catling, A. D., Pfister, K. K., 2012. Trk activation of the ERK1/2 kinase pathway stimulates intermediate chain phosphorylation and recruits cytoplasmic dynein to signaling endosomes for retrograde axonal transport. The Journal of neuroscience: the official journal of the Society for Neuroscience 32, 15495-15510; Song, E. J., Yoo, Y. S., 2011. Nerve growth factor-induced neurite outgrowth is potentiated by stabilization of TrkA receptors. BMB reports 44, 182-186] into endosomes with Rab22GTPase [Id.; also Wang, L., Liang, Z., Li, G., 2011. Rab22 controls NGF signaling and neurite outgrowth in PC12 cells. Molecular biology of the cell 22, 3853-3860] and activation of pERK (1/2)/cAMP, [Chen, J. H., Lee, D. C., Chiu, I. M., 2014. Cytotoxic effects of acrylamide in nerve growth factor or fibroblast growth factor 1-induced neurite outgrowth in PC12 cells. Archives of toxicology 88, 769-780; Nishina, A., Kimura, H., Tsukagoshi, H., Kozawa, K., Koketsu, M., Ninomiya, M., Sato, D., Obara, Y., Furukawa, S., 2013. Neurite outgrowth of PC12 cells by 4'-O-beta-D-glucopyranosyl-3',4-dimethoxychalcone from *Brassica rapa* L. 'hidabeni' was enhanced by pretreatment with p38MAPK inhibitor. Neurochemical research 38, 2397-2407; Terada, K., Kojima, Y., Watanabe, T., Izumo, N., Chiba, K., Karube, Y., 2014. Inhibition of nerve growth factor-induced neurite outgrowth from PC12 cells by dexamethasone: signaling pathways through the glucocorticoid receptor and phosphorylated Akt and ERK1/2. PloS one 9, e93223; Thauerer, B., Voegele, P., Hermann-Kleiter, N., Thuille, N., de Araujo, M. E., Offterdinger, M., Baier, G., Huber, L. A., Baier-Bitterlich, G., 2014. LAMTOR2-mediated modulation of NGF/MAPK activation kinetics during differentiation of PC12 cells. PloS one 9, e95863] protein kinase A, pCREB signaling [Id.] causing mass change in microtubule proteins. [Nielander, H. B., French, P., Oestreicher, A. B., Gispen, W. H., Schotman, P., 1993. Spontaneous morphological changes by overexpression of the growth-associated protein B-50/GAP-43 in a PC12 cell line.

Neuroscience letters 162, 46-50; Pradines, A., Magazin, M., Schiltz, P., Le Fur, G., Caput, D., Ferrara, P., 1995. Evidence for nerve growth factor-potentiating activities of the non-peptidic compound SR 57746A in PC12 cells. Journal of neurochemistry 64, 1954-1964] These events evoke a sustained cytoskeletal reorganization/elongation, formation of neuritic shafts which are embodied by filopodia/lamellipodia growth cones that extend along a biological matrix such as collagen. [Aletta, J. M., Greene, L. A., 1988. Growth cone configuration and advance: a time-lapse study using video-enhanced differential interference contrast microscopy. The Journal of neuroscience: the official journal of the Society for Neuroscience 8, 1425-1435; Nuttall, R. P., Zinsmeister, P. P., 1983. Differential response to contact during embryonic nerve-nonnerve cell interactions. Cell motility 3, 307-320; Robbins, N., Polak, J., 1988. Filopodia, lamellipodia and retractions at mouse neuromuscular junctions. Journal of neurocytology 17, 545-561] Neurite outgrowth is a gradual process that occurs through retraction and polymerizing of F-actin [Nielander et al., 1993; Pradines et al., 1995] aided by numerous proteins such as Arp2/3, ccdc8, cortactin, GAP-43 or syntaxin 6. [Kabayama, H., Tokushige, N., Takeuchi, M., Mikoshiba, K., 2008. Syntaxin 6 regulates nerve growth factor-dependent neurite outgrowth. Neuroscience letters 436, 340-344; Spillane, M., Ketschek, A., Donnelly, C. J., Pacheco, A., Twiss, J. L., Gallo, G., 2012. Nerve growth factor-induced formation of axonal filopodia and collateral branches involves the intra-axonal synthesis of regulators of the actin-nucleating Arp2/3 complex. The Journal of neuroscience: the official journal of the Society for Neuroscience 32, 17671-17689; Zhang et al., 2014]

With growing interest in complementary and alternative medicines, the current inventors recently conducted a high throughput screening to determine if any food based nutraceutical has the capacity to act as a NGF mimetic. [Mazzio, E., Georges, B., McTier, O., Soliman, K. F., 2015. Neurotrophic Effects of Mu Bie Zi (*Momordica cochinchinensis*) Seed Elucidated by High-Throughput Screening of Natural Products for NGF Mimetic Effects in PC-12 Cells. Neurochemical research 40, 2102-2112] The results showed only one natural product of over 1100 tested with capacity to act as a NGF mimetic: Mu Bie Zi, *Momordica cochinchinensis* seeds. There are numerous studies reporting tissue and organ protective effects of *Momordica charantia* (albeit not seed pit specific) in diabetic models where administration can normalize kidney function, enhance antioxidant enzyme systems, glutathione peroxidase, superoxide dismutase, catalase levels and heme oxygenase-1 [Raish, M., Ahmad, A., Jan, B. L., Alkharfy, K. M., Ansari, M. A., Mohsin, K., Jenoobi, F. A., Al-Mohizea, A., 2016. *Momordica charantia* polysaccharides mitigate the progression of STZ induced diabetic nephropathy in rats. International journal of biological macromolecules 91, 394-399; Sathishsekar, D., Subramanian, S., 2005. Antioxidant properties of *Momordica Charantia* (bitter gourd) seeds on Streptozotocin induced diabetic rats. Asia Pacific journal of clinical nutrition 14, 153-158] increase insulin sensitivity [Wang, L., Liang, Z., Li, G., 2011. Rab22 controls NGF signaling and neurite outgrowth in PC12 cells. Molecular biology of the cell 22, 3853-3860] reduce hyperglycemia-induced cardiac fibrosis [Abas, R., Othman, F., Thent, Z. C., 2014. Protective effect of *Momordica charantia* fruit extract on hyperglycaemia-induced cardiac fibrosis. Oxidative medicine and cellular longevity 2014, 429060] and cataracts. [Rathi, S. S., Grover, J. K., Vikrant, V., Biswas, N. R., 2002. Prevention of experimental diabetic cataract by Indian Ayurvedic plant extracts. Phytotherapy research: PTR 16, 774-777] Other tissue restorative effects of diverse plants under *Momordica* species have been reported such as the anti-hyperglycemic mcy protein in *Momordica cymbalaria* [Marella, S., Maddirela, D. R., Badri, K. R., Jyothi Kumar, M. V., Chippada, A., 2015. Antihyperlipidemic and biochemical activities of Mcy protein in streptozotocin induced diabetic rats. Cellular physiology and biochemistry: international journal of experimental cellular physiology, biochemistry, and pharmacology 35, 1326-1334]; or constituents of *Momordica dioica* being protective against liver, kidney, and pancreas damage in severe diabetic rats. [Sharma, P., Singh, R., 2014. Effect of *Momordica dioica* fruit extract on antioxidant status in liver, kidney, pancreas, and serum of diabetic rats. Pharmacognosy research 6, 73-79]. Although few studies have evaluated the actually seed pit, some show its capacity to attenuate cisplatin-induced kidney damage [Jung, K., Lee, D., Yu, J. S., Namgung, H., Kang, K. S., Kim, K. H., 2016. Protective effect and mechanism of action of saponins isolated from the seeds of gac (*Momordica cochinchinensis* Spreng.) against cisplatin-induced damage in LLC-PK1 kidney cells. Bioorganic & medicinal chemistry letters 26, 1466-1470] and gastric ulcers pathologies. [Jo, H. J., Kim, N., Nam, R. H., Chang, H., Kim, J. H., Park, J. H., Kang, J. M., Lee, D. H., Jung, H. C., 2013. The Effect of Cochinchina *momordica* Seed Extract on Gastric Acid Secretion and Morphologic Change in Aged Rat Stomach. Gut and liver 7, 560-568; Jung, K., Chin, Y. W., Chung, Y. H., Park, Y. H., Yoo, H., Min, D. S., Lee, B., Kim, J., 2013. Anti-gastritis and wound healing effects of Momordicae Semen extract and its active component. Immunopharmacology and immunotoxicology 35, 126-132]

NGF signaling by a mimetic is likely to induce cellular reorganization/elongation of cytoskeletal microtubules (formation of neuritic shafts) and development of filopodia/lamellipodia with flexible growth cones that extend along a biological matrix (e.g., collagen). [Nuttall R P, Zinsmeister P P. Differential response to contact during embryonic nerve-nonnerve cell interactions. Cell Motil. 1983; 3:307-320; Aletta J M, Greene L A. Growth cone configuration and advance: a time-lapse study using video-enhanced differential interference contrast microscopy. J Neurosci. 1988; 8:1425-1435; Robbins N, Polak J. Filopodia, lamellipodia and retractions at mouse neuromuscular junctions. J Neurocytol. 1988; 17:545-561]

Internal signaling associated with these outward manifestations include phosphorylation of tropomyosin-related kinase receptor (Trk) (A-C), the subsequent early rise in pERK (1/2)/cAMP signaling, late phase endosomal internalization of the TrKA receptor complex [Mitchell D J, Blasier K R, Jeffery E D, Ross M W, Pullikuth A K, Suo D, Park J, Smiley W R, Lo K W, Shabanowitz J, Deppmann C D, Trinidad J C, Hunt D F, Catling A D, Pfister K K. Trk activation of the ERK1/2 kinase pathway stimulates intermediate chain phosphorylation and recruits cytoplasmic dynein to signaling endosomes for retrograde axonal transport. J Neurosci. 2012; 32:15495-15510; Mitchell D J, Blasier K R, Jeffery E D, Ross M W, Pullikuth A K, Suo D, Park J, Smiley W R, Lo K W, Shabanowitz J, Deppmann C D, Trinidad J C, Hunt D F, Catling A D, Pfister K K. Trk activation of the ERK1/2 kinase pathway stimulates intermediate chain phosphorylation and recruits cytoplasmic dynein to signaling endosomes for retrograde axonal transport. J Neurosci. 2012; 32:15495-15510; Abu El-Asrar A M, Mohammad G, De Hertogh G, Nawaz M I, Van Den Eynde K, Siddiquei M M, Struyf S, Opdenakker G, Geboes K. Neurotrophins and neurotrophin receptors in proliferative diabetic retinopathy. PLoS One. 2013; 8:e65472; Arimura N, Kimura T, Nakamuta S, Taya S, Funahashi Y, Hattori A, Shimada A, Menager C, Kawabata S, Fujii K, Iwamatsu A, Segal R A, Fukuda M, Kaibuchi K. Anterograde transport of TrkB in axons is mediated by direct interaction with Slp1 and Rab27. Dev Cell. 2009; 16:675-686] and stimulation of microtubule binding proteins which act on tubulin polymers, F-actin microfilaments and G-actin tetramers. [Pradines A, Magazin M, Schiltz P, Le Fur G, Caput D, Ferrara P. Evidence for nerve growth factor-potentiating activities of the nonpeptidic compound SR 57746A in PC12 cells. J Neurochem. 1995; 64:1954-1964; Nielander H B, French P, Oestreicher A B, Gispen W H, Schotman P. Spontaneous morphological changes by overexpression of the growth-associated protein B-50/GAP-43 in a PC12 cell line. Neurosci Lett. 1993; 162:46-50]

Likewise, research throughout the literature is fairly consistent reporting the NGF invoked rise in pERK1/2 [Thauerer B, Voegele P, Hermann-Kleiter N, Thuille N, de Araujo M E, Offterdinger M, Baier G, Huber L A, Baier-Bitterlich G. LAMTOR2-mediated modulation of NGF/MAPK activation kinetics during differentiation of PC12 cells. PLoS One. 2014; 9:e95863; Chen J H, Lee D C, Chiu I M. Cytotoxic effects of acrylamide in nerve growth factor or fibroblast growth factor 1-induced neurite outgrowth in PC12 cells. Arch Toxicol. 2014; 88:769-780; Terada K, Kojima Y, Watanabe T, Izumo N, Chiba K, Karube Y. Inhibition of nerve growth factor-induced neurite outgrowth from PC12 cells by dexamethasone: signaling pathways through the glucocorticoid receptor and phosphorylated Akt and ERK1/2. PLoS One. 2014; 9:e93223; Nishina A, Kimura H, Tsukagoshi H, Kozawa K, Koketsu M, Ninomiya M, Sato D, Obara Y, Furukawa S. Neurite outgrowth of PC12 cells by 4'-O-beta-D-glucopyranosyl-3',4-dimethoxychalcone from *Brassica rapa* L. 'hidabeni' was enhanced by pretreatment with p38MAPK inhibitor. Neurochem Res. 2013; 38:2397-2407], and pAKT [Chen J H, Lee D C, Chiu I M. Cytotoxic effects of acrylamide in nerve growth factor or fibroblast growth factor 1-induced neurite outgrowth in PC12 cells. Arch Toxicol. 2014; 88:769-780; Terada K, Kojima Y, Watanabe T, Izumo N, Chiba K, Karube Y. Inhibition of nerve growth factor-induced neurite outgrowth from PC12 cells by dexamethasone: signaling pathways through the glucocorticoid receptor and phosphorylated Akt and ERK1/2. PLoS One. 2014; 9:e93223; Nishina A, Kimura H, Tsukagoshi H, Kozawa K, Koketsu M, Ninomiya M, Sato D, Obara Y, Furukawa S. Neurite outgrowth of PC12 cells by 4'-O-beta-D-glucopyranosyl-3',4-dimethoxychalcone from *Brassica rapa* L. 'hidabeni' was enhanced by pretreatment with p38MAPK inhibitor. Neurochem Res. 2013; 38:2397-2407], as well as cAMP [Chijiwa T, Mishima A, Hagiwara M, Sano M, Hayashi K, Inoue T, Naito K, Toshioka T, Hidaka H. Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-89), of PC12D pheochromocytoma cells. J Biol Chem. 1990; 265:5267-5272; Emery A C, Eiden M V, Eiden L E. Separate cyclic AMP sensors for neuritogenesis, growth arrest, and survival of neuroendocrine cells. J Biol Chem. 2014; 289:10126-10139], protein kinase A, pCREB [Thauerer B, Voegele P, Hermann-Kleiter N, Thuille N, de Araujo M E, Offterdinger M, Baier G, Huber L A, Baier-Bitterlich G. LAMTOR2-mediated modulation of NGF/MAPK activation kinetics during differentiation of PC12 cells. PLoS One. 2014; 9:e95863; Chen J H, Lee D C, Chiu I M. Cytotoxic effects of acrylamide in nerve growth factor or fibroblast growth factor 1-induced neurite outgrowth in PC12 cells. Arch Toxicol. 2014; 88:769-780; Terada K, Kojima Y, Watanabe T, Izumo N, Chiba K, Karube Y. Inhibition of nerve growth factor-induced neurite outgrowth from PC12 cells by dexamethasone: signaling pathways through the glucocorticoid receptor and phosphorylated Akt and ERK1/2. PLoS One. 2014; 9:e93223; Nishina A, Kimura H, Tsukagoshi H, Kozawa K, Koketsu M, Ninomiya M, Sato D, Obara Y, Furukawa S. Neurite outgrowth of PC12 cells by 4'-O-beta-D-glucopyranosyl-3',4-dimethoxychalcone from *Brassica rapa* L. 'hidabeni' was enhanced by pretreatment with p38MAPK inhibitor. Neurochem Res. 2013; 38:2397-2407] with inconsistent reports for p38MAPK [Nishina A, Kimura H, Tsukagoshi H, Kozawa K, Koketsu M, Ninomiya M, Sato D, Obara Y, Furukawa S. Neurite outgrowth of PC12 cells by 4'-O-beta-D-glucopyranosyl-3',4-dimethoxychalcone from *Brassica rapa* L. 'hidabeni' was enhanced by pretreatment with p38MAPK inhibitor. Neurochem Res. 2013; 38:2397-2407].

While rapid early signaling events control the initial impact of NGF, clearly neurite outgrowth is a lengthy process in PC-12 cells—occurring over a 3-7 day period. It is believed that long term signaling effects involve NGF-TrkA endocytosis into endosomes with Rab22GTPase [Mitchell D J, Blasier K R, Jeffery E D, Ross M W, Pullikuth A K, Suo D, Park J, Smiley W R, Lo K W, Shabanowitz J, Deppmann C D, Trinidad J C, Hunt D F, Catling A D, Pfister K K. Trk activation of the ERK1/2 kinase pathway stimulates intermediate chain phosphorylation and recruits cytoplasmic dynein to signaling endosomes for retrograde axonal transport. J Neurosci. 2012; 32:15495-15510; Song E J, Yoo Y S. Nerve growth factor-induced neurite outgrowth is potentiated by stabilization of TrkA receptors. BMB Rep. 2011; 44:182-186; Abu El-Asrar A M, Mohammad G, De Hertogh G, Nawaz M I, Van Den Eynde K, Siddiquei M M, Struyf S, Opdenakker G, Geboes K. Neurotrophins and neurotrophin receptors in proliferative diabetic retinopathy. PLoS One. 2013; 8:e65472; Arimura N, Kimura T, Nakamuta S, Taya S, Funahashi Y, Hattori A, Shimada A, Menager C, Kawabata S, Fujii K, Iwamatsu A, Segal R A, Fukuda M, Kaibuchi K. Anterograde transport of TrkB in axons is mediated by direct interaction with Slp1 and Rab27. Dev Cell. 2009; 16:675-686; Wang L, Liang Z, Li G. Rab22 controls NGF signaling and neurite outgrowth in PC12 cells. Mol Biol Cell. 2011; 22:3853-3860] and a stabilizing protein such as coronin-1 [Suo D, Park J, Harrington A W, Zweifel L S, Mihalas S, Deppmann C D. Coronin-1 is a neurotrophin endosomal effector that is required for developmental competition for survival. Nat Neurosci. 2014; 17:36-45], which can then initiate restructure of the membrane cytoskeleton in conjunction Rho GTPase Rac 1, cdc42 and Tc10 [Fujita A, Koinuma S, Yasuda S, Nagai H, Kamiguchi H, Wada N, Nakamura T. GTP hydrolysis of TC10 promotes neurite outgrowth through exocytic fusion of Rab11- and L1-containing vesicles by releasing exocyst component Exo70. PLoS One. 2013; 8:e79689; Pommereit D, Wouters F S. An NGF-induced Exo70-TC10 complex locally antagonises Cdc42-mediated activation of N-WASP to modulate neurite outgrowth. J Cell Sci. 2007; 120:2694-2705].

These processes are believed to be important to initial formations of lamellipodia, filopodia or stress fibers. [Nuttall R P, Zinsmeister P P. Differential response to contact during embryonic nerve-nonnerve cell interactions. Cell Motil. 1983; 3:307-320; Aletta J M, Greene L A. Growth cone configuration and advance: a time-lapse study using video-enhanced differential interference contrast microscopy. J Neurosci. 1988; 8:1425-1435; Robbins N, Polak J. Filopodia, lamellipodia and retractions at mouse neuromuscular junctions. J Neurocytol. 1988; 17:545-561], which are subject to retraction and polymerizing of F-actin involved with neurite outgrowth [Pradines A, Magazin M, Schiltz P, Le Fur G, Caput D, Ferrara P. Evidence for nerve growth factor-potentiating activities of the nonpeptidic compound SR 57746A in PC12 cells. J Neurochem. 1995; 64:1954-1964; Nielander H B, French P, Oestreicher A B, Gispen W H, Schotman P. Spontaneous morphological changes by over-expression of the growth-associated protein B-50/GAP-43 in a PC12 cell line. Neurosci Lett. 1993; 162:46-50]. In addition, there are hundreds of actin binding proteins (ABPs) that assist in this process, with specific roles in F-actin crosslinking, severing, polymerization (growth), retraction and end capping at the growth cones. ABP concentrations highly abundant in growth cones consists of Arp2/3, ccdc8, cortactin, GAP-43 or syntaxin 6 [Kabayama H, Tokushige N, Takeuchi M, Mikoshiba K. Syntaxin 6 regulates nerve growth factor-dependent neurite outgrowth. Neurosci Lett. 2008; 436:340-344] responsible for neurite extension elongation [Zhang H, Wu F, Kong X, Yang J, Chen H, Deng L, Cheng Y, Ye L, Zhu S, Zhang X, Wang Z, Shi H, Fu X, Li X, Xu H, Lin L, Xiao J. Nerve growth factor improves functional recovery by inhibiting endoplasmic reticulum stress-induced neuronal apoptosis in rats with spinal cord injury. J Transl Med. 2014; 12:130; Spillane M, Ketschek A, Donnelly C J, Pacheco A, Twiss J L, Gallo G. Nerve growth factor-induced formation of axonal filopodia and collateral branches involves the intra-axonal synthesis of regulators of the actin-nucleating Arp2/3 complex. J Neurosci. 2012; 32:17671-17689]. Other wide type extensions often observed in NGF-treated PC12 cells termed "varicones" are concentrated in proteins such as synaptophysin, calpain2, syntaxin. [Mingorance-Le Meur A, Mohebiany A N, O'Connor T P. Varicones and growth cones: two neurite terminals in PC12 cells. PLoS One. 2009; 4:e4334].

It is known that MCS seeds are orange/red in color due to lycopene [Phan-Thi H, Wache Y. Isomerization and increase in the antioxidant properties of lycopene from *Momordica cochinchinensis* (gac) by moderate heat treatment with UV-Vis spectra as a marker. Food Chem. 2014; 156:58-63; Aoki H, Kieu N T, Kuze N, Tomisaka K, Van Chuyen N. Carotenoid pigments in GAC fruit (*Momordica cochinchinensis* SPRENG) Biosci Biotechnol Biochem. 2002; 66:2479-2482] and it has significant concentrations of triterpenoidal saponins, gypsogenin and quillaic acid glycosides [Jung K, Chin Y W, Yoon K, Chae H S, Kim C Y, Yoo H, Kim J. Anti-inflammatory properties of a triterpenoidal glycoside from *Momordica cochinchinensis* in LPS-stimulated macrophages. Immunopharmacol Immunotoxicol. 2013; 35:8-14], and low MW cell penetrating dipeptides [Ng T B, Chan W Y, Yeung H W. Proteins with abortifacient, ribosome inactivating, immunomodulatory, antitumor and anti-AIDS activities from Cucurbitaceae plants. Gen Pharmacol. 1992; 23:579-590] such as cochinin B (28 kDa) [Wong K L, Wong R N, Zhang L, Liu W K, Ng T B, Shaw P C, Kwok P C, Lai Y M, Zhang Z J, Zhang Y, Tong Y, Cheung H P, Lu J, Sze S C. Bioactive proteins and peptides isolated from Chinese medicines with pharmaceutical potential. Chin Med. 2014; 9:19] and *M. cochinchinensis* trypsin inhibitor I (MCoTI-I) and 2 (MCoTI-II). [D'Souza C, Henriques S T, Wang C K, Craik D J. Structural parameters modulating the cellular uptake of disulfide-rich cyclic cell-penetrating peptides: MCoTI-II and SFTI-1. Eur J Med Chem. 2014; 88:10-18] MCoTI-II belongs to the cyclotide family of plant-derived cyclic peptides that are characterized by a cyclic cystine knot motif [Cascales L, Henriques S T, Kerr M C, Huang Y H, Sweet M J, Daly N L, Craik D J. Identification and characterization of a new family of cell-penetrating peptides: cyclic cell-penetrating peptides. J Biol Chem. 2011; 286:36932-36943; Chan L Y, He W, Tan N, Zeng G, Craik D J, Daly N L. A new family of cystine knot peptides from the seeds of *Momordica cochinchinensis*. Peptides. 2013; 39:29-35] known to be thermally and chemically stable, and resistant to enzymatic degradation [Craik D J, Simonsen S, Daly N L. The cyclotides: novel macrocyclic peptides as scaffolds in drug design. Curr Opin Drug Discov Dev. 2002; 5:251-260; Park S, Stromstedt A A, Goransson U. Cyclotide structure-activity relationships: qualitative and quantitative approaches linking cytotoxic and anthelmintic activity to the clustering of physicochemical forces. PLoS One. 2014; 9:e91430]. MCS derived cyclic knottins share similar conformational form as noncyclic squash inhibitors, such as CPTI [Heitz A, Hernandez J F, Gagnon J, Hong T T, Pham T T, Nguyen T M, Le-Nguyen D, Chiche L. Solution structure of the squash trypsin inhibitor MCoTI-II. A new family for cyclic knottins. Biochemistry. 2001; 40:7973-7983] and interesting also, NGF [Kliemannel M, Weininger U, Balbach J, Schwarz E, Rudolph R. Examination of the slow unfolding of pro-nerve growth factor argues against a loop threading mechanism for nerve growth factor. Biochemistry. 2006; 45:3517-3524]. While NGF medicinal applications are limited, natural NGF mimetics such as those found in the MCS extract are generally robust in therapeutic properties previously reported to have anti-viral, [Oyuntseteg N, Khasnatinov M A, Molor-Erdene P, Oyunbileg J, Liapunov A V, Danchinova G A, Oldokh S, Baigalmaa J, Chimedragchaa C. Evaluation of direct antiviral activity of the Deva-5 herb formulation and extracts of five Asian plants against influenza A virus H3N8. BMC Complement Altern Med. 2014; 14:235; Thongyoo P, Roque-Rosell N, Leatherbarrow R J, Tate E W. Chemical and biomimetic total syntheses of natural and engineered MCoTI cyclotides. Org Biomol Chem. 2008; 6:1462-1470] anti-angiogenic, anti-tumor [Zheng L, Zhang Y M, Zhan Y Z, Liu C X. *Momordica cochinchinensis* seed extracts suppress migration and invasion of human breast cancer ZR-75-30 cells via down-regulating MMP-2 and MMP-9. Asian Pac J Cancer Prev. 2014; 15:1105-1110] anti-inflammatory and anti-oxidant properties [Wong K L, Wong R N, Zhang L, Liu W K, Ng T B, Shaw P C, Kwok P C, Lai Y M, Zhang Z J, Zhang Y, Tong Y, Cheung H P, Lu J, Sze S C. Bioactive proteins and peptides isolated from Chinese medicines with pharmaceutical potential. Chin Med. 2014; 9:19] and an ability to enhance innate immunity [Rajput Z I, Xiao C W, Hu S H, Habib M, Soomro N A. Enhancement of immune responses to infectious bursal disease vaccine by supplement of an extract made from *Momordica cochinchinensis* (Lour.) Spreng. seeds. Poult Sci. 2010; 89:1129-1135; Tsoi A Y, Ng T B, Fong W P. Immunomodulatory activity of a chymotrypsin inhibitor from *Momordica cochinchinensis* seeds. J Pept Sci. 2006; 12:605-611], aid in wound healing [Jung K, Chin Y W, Chung Y H, Park Y H, Yoo H, Min D S, Lee B, Kim J. Anti-gastritis and wound healing effects of Momordicae Semen extract and its active component. Immunopharmacol Immunotoxicol. 2013; 35:126-132] and heal gastric ulcers. [Kang J M, Kim N, Kim B, Kim J H, Lee B Y, Park J H, Lee M K, Lee H S, Kim J S, Jung H C, Song I S. Enhancement of gastric ulcer healing and angiogenesis by cochinchina Momordica seed extract in rats. J Korean Med Sci. 2010; 25:875-881].

Standard treatments for neurodegenerative disorders such as Alzheimer's disease (AD), Parkinson's disease (PD), amyotrophic lateral sclerosis and Huntington's disease restore the balance of neurotransmitters enabling somewhat normal neuromotor function. While most drug regimens have capacity to improve quality of life, they do not address the underlying etiology of the disease and thereby do not arrest progression degenerative processes. Although endogenous synthesis of trophic molecules such as NGF [Levi-Montalcini R, Cohen S. In vitro and in vivo effects of a nerve growth-stimulating agent isolated from snake venom. Proc Natl Acad Sci USA. 1956; 42:695-699], brain-derived neurotrophic factor (BDNF) and neurotrophin-3/neurotrophin-4 can elicit CNS neuronal differentiation and can effectively stimulate neuronal growth/repair [Esmaeili A, Alifarj a S, Nourbakhsh N, Talebi A. Messenger RNA expression patterns of neurotrophins during transdifferentiation of stem cells from human-exfoliated deciduous teeth into neural-like cells. Avicenna J Med Biotechnol. 2014; 6:21-26; Bothwell M. NGF, BDNF, NT3, and NT4. Handb Exp Pharmacol. 2014; 220:3-15], therapeutic applications are limited by a wide range of negative pathogenic side effects such as neuropathic pain [Pezet S. Neurotrophins and pain. Biol Aujourd'hui. 2014; 208:21-29; Muralidharan A, Wyse B D, Smith M T. Analgesic efficacy and mode of action of a selective small molecule angiotensin II type 2 receptor antagonist in a rat model of prostate cancer-induced bone pain. Pain Med. 2014; 15:93-110], bladder/urinary pain [Kim S W, Im Y J, Choi H C, Kang H J, Kim J Y, Kim J H. Urinary nerve growth factor correlates with the severity of urgency and pain. Int Urogynecol J. 2014; 25:1561-1567], itchy skin (pruritus) atopic dermatitis [Ono R, Kagawa Y, Takahashi Y, Akagi M, Kamei C. Effect of 2,3,7,8-tetrachlorodibenzo-p-dioxin on scratching behavior in mice. Int Immunopharmacol. 2010; 10:304-307; Yosipovitch G. Dry skin and impairment of barrier function associated with itch—new insights. Int J Cosmet Sci. 2004; 26:1-7; Teresiak-Mikolajczak E, Czarnecka-Operacz M, Jenerowicz D, Silny W. Neurogenic markers of the inflammatory process in atopic dermatitis: relation to the severity and pruritus. Postepy Dermatologii i Alergologii. 2013; 30:286-292], deep tissue tenderness [McMahon S B, Cafferty W B, Marchand F. Immune and glial cell factors as pain mediators and modulators. Exp Neurol. 2005; 192:444-462; Bannwarth B, Kostine M. Targeting nerve growth factor (NGF) for pain management: what does the future hold for NGF antagonists? Drugs. 2014; 74:619-626], exacerbated inflammatory conditions such as arthritis, asthma [McMahon S B, Cafferty W B, Marchand F. Immune and glial cell factors as pain mediators and modulators. Exp Neurol. 2005; 192:444-462; Kim J S, Kang J Y, Ha J H, Lee H Y, Kim S J, Kim S C, Ahn J H, Kwon S S, Kim Y K, Lee S Y. Expression of nerve growth factor and matrix metallopeptidase-9/tissue inhibitor of metalloproteinase-1 in asthmatic patients. J Asthma: Off J Assoc Care Asthma. 2013; 50:712-717; Chen Y L, Huang H Y, Lee C C, Chiang B L. Small interfering RNA targeting nerve growth factor alleviates allergic airway hyperresponsiveness. Mol Ther Nucleic Acids. 2014; 3:e158], intervertebral disc degeneration [Kao T H, Peng Y J, Tsou H K, Salter D M, Lee H S. Nerve growth factor promotes expression of novel genes in intervertebral disc cells that regulate tissue degradation. J Neurosurg Spinel-9Spine. 2014; 21:653-656] and cancer [Vinores S A, Perez-Polo J R. Nerve growth factor and neural oncology. J Neurosci Res. 1983; 9:81-100; Wang W, Chen J, Guo X. The role of nerve growth factor and its receptors in tumorigenesis and cancer pain. Biosci Trends. 2014; 8:68-74; Hondermarck H. Neurotrophins and their receptors in breast cancer. Cytokine Growth Factor Rev. 2012; 23:357-365]. Therefore, there is a need for identification of small MW neurotrophic compounds that may have therapeutic value in treatment of peripheral/CNS injury or neurodegenerative disorders, without the limitations of endogenous neurotrophins.

Furthermore, elevated levels of NGF in various neuronal tissue can lead to behavioral/cognitive disorders such as autism [Dincel N, Unalp A, Kutlu A, Ozturk A, Uran N, Ulusoy S. Serum nerve growth factor levels in autistic children in Turkish population: a preliminary study. Indian J Med Res. 2013; 138:900-903], bipolar [Barbosa I G, Huguet R B, Neves F S, Reis H J, Bauer M E, Janka Z, Palotas A, Teixeira A L. Impaired nerve growth factor homeostasis in patients with bipolar disorder. World J Biol Psychiatry. 2011; 12:228-232] and attention deficit/hyperactivity disorder. [Guney E, Ceylan M F, Kara M, Tekin N, Goker Z, Senses Dinc G, Ozturk O, Eker S, Kizilgun M. Serum nerve growth factor (NGF) levels in children with attention deficit/hyperactivity disorder (ADHD) Neurosci Lett. 2014; 560:107-111]

Given the adverse systemic effects of NGF, in addition to its limited BBB transport [Backman C, Rose G M, Hoffer B J, Henry M A, Bartus R T, Friden P, Granholm A C. Systemic administration of a nerve growth factor conjugate reverses age-related cognitive dysfunction and prevents cholinergic neuron atrophy. J Neurosci. 1996; 16:5437-5442; Poduslo J F, Curran G L. Permeability at the blood-brain and blood-nerve barriers of the neurotrophic factors: NGF, CNTF, NT-3, BDNF. Brain Res Mol Brain Res. 1996; 36:280-286] and associated peripheral neuropathies, oral administration is not feasible. For that reason, research focus on the use of NGF application is largely limited to its use in genetically modified mesenchymal stem cell transplants [Cui X, Chen L, Ren Y, Ji Y, Liu W, Liu J, Yan Q, Cheng L, Sun Y E. Genetic modification of mesenchymal stem cells in spinal cord injury repair strategies. Biosci Trends. 2013; 7:202-208], artificial biomaterial 3D nerve guidance systems/composites [Kuihua Z, Chunyang W, Cunyi F, Xiumei M. Aligned SF/P(LLA-CL)-blended nanofibers encapsulating nerve growth factor for peripheral nerve regeneration. J Biomed Mater Res, Part A. 2014; 102:2680-2691] or NGF liposomal-targeted drug delivery systems (i.e., embedded within targeted delivery nano-particle drug systems) to effectively treat CNS/PNS injuries. [Kuo Y C, Wang C T. Protection of SK-N-MC cells against beta-amyloid peptide-induced degeneration using neuron growth factor-loaded liposomes with surface lactoferrin. Biomaterials. 2014; 35:5954-5964; Yu H, Liu J, Ma J, Xiang L. Local delivery of controlled released nerve growth factor promotes sciatic nerve regeneration after crush injury. Neurosci Lett. 2014; 566:177-181].

There is a need for research efforts in the identification and development of small molecule NGF mimetics, which could potentially pass through the BBB and exert neurotrophic effects within the CNS, without side effect. To date, there are only a few known NGF mimetics such as GK-2 h, which in experimental models show capacity to promote neuronal survival, differentiation and synaptic plasticity demonstrating possible application for Alzheimer's disease [Povarnina P Y, Vorontsova O N, Gudasheva T A, Ostrovskaya R U, Seredenin S B. Original nerve growth factor mimetic dipeptide GK-2 restores impaired cognitive functions in rat models of Alzheimer's disease. Acta Naturae. 2013; 5:84-91], Parkinson's disease [Antipova T A, Gudasheva T A, Seredenin S B. In vitro study of neuroprotective properties of GK-2, a new original nerve growth factor mimetic. Bull Exp Biol Med. 2011; 150:607-609], cerebral ischemia [Povarina P, Gudasheva T A, Vorontsova O N, Nikolaev S V, Antipova T A, Ostrovskaia R U, Seredin S B.

Neuroprotective effects of a dipeptide mimetic on the GK-2 nerve growth factor in model of permanent common carotid artery occlusion in rats. Eksperimental'naia i Klinicheskaia Farmakologiia. 2012; 75:15-20], neural toxicity [Zhao G Y, Ding X D, Guo Y, Chen W M. Intrathecal lidocaine neurotoxicity: combination with bupivacaine and ropivacaine and effect of nerve growth factor. Life Sci. 2014; 112:10-21], or brain/spinal cord injury [Zhang H, Wu F, Kong X, Yang J, Chen H, Deng L, Cheng Y, Ye L, Zhu S, Zhang X, Wang Z, Shi H, Fu X, Li X, Xu H, Lin L, Xiao J. Nerve growth factor improves functional recovery by inhibiting endoplasmic reticulum stress-induced neuronal apoptosis in rats with spinal cord injury. J Transl Med. 2014; 12:130].

Accordingly, what is needed is small molecule NGF mimetics that can penetrate the BBB and initiate CNS neuronal outgrowth/regeneration. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

The long-standing but heretofore unfulfilled need for an improved treatment for CNS diseases is now met by a new, useful, and nonobvious invention.

In an embodiment, the current invention is a composition for preventing or treating a central nervous system disease (e.g., Alzheimer's disease, Parkinson's disease, etc.), comprising *Momordica cochinchinensis* seed extract in a pharmaceutically effective carrier. The seed extract may be a total plant protein isolate, and the extract includes *Momordica cochinchinensis* trypsin inhibitor II.

In a separate embodiment, the current invention is a method of preventing or treating a central nervous system disease (e.g., Alzheimer's disease, Parkinson's disease, etc.) in a patient, or a symptom thereof by inducing neurite outgrowth in the patient. The method includes administering a therapeutically effective amount of *Momordica cochinchinensis* seed extract to the patient suffering from the central nervous system disease. This treatment/prevention of the disease may be accomplished by reducing or halting progression of neuronal damage associated with the disease. The seed extract may be a total plant protein isolate, and the extract includes *Momordica cochinchinensis* trypsin inhibitor II. In an embodiment, the therapeutically effective amount of the extract can have a concentration of less than about 200 µg/mL, or more specifically less than about 150 µg/mL.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 8A is a sample image of the control.

FIG. 8B is a sample image of NGF.

FIG. 8C is a sample image of the protein isolation reagent blank control.

FIG. 8D is a sample image of methanol.

FIG. 8E is a sample image of acetone.

FIG. 8F is a sample image of protein isolate 0.02 mg/mL.

FIG. 8G is a sample image of ethanol.

FIG. 8H is a sample image of ethyl acetate.

FIG. 8I is a sample image of ether.

FIG. 8J is a sample image of original crude MCS aqueous extract 0.2 mg/mL. Overall, FIGS. 8A-8J depict bioactivity guided chemical and protein fractionation in determination of active NGF mimetic constituents of MCS seed.

DETAILED DESCRIPTION

In the following detailed description, reference is made to the accompanying drawings, which form a part thereof, and within which are shown by way of illustration specific embodiments by which the invention may be practiced. It is to be understood that other embodiments may be used and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In an embodiment, the claimed subject matter includes small molecule NGF mimetics that can penetrate the BBB and initiate CNS neuronal outgrowth/regeneration. It is an object of the present application to develop a treatment/prevention strategy for Parkinson's disease AD and PD, among other neurodegenerative diseases, by incorporation of novel elements including neurotrophins. Neurite outgrowth/regeneration is a strong indicator of a treatment mechanism for AD and PD, both of which include symptoms of neurodegeneration. As such, it is contemplated herein that a positive effect on neurite growth is enabling of a treatment composition and methodology for AD and PD.

Study 1—Identification of NGF Mimetic

Generally, the object of this study was to screen a large variety of natural plant extracts and polyphenolics to reveal substances that exert NGF mimetic effects in rat dopaminergic pheochromocytoma PC-12 cells on collagen-coated plates. The study focuses on the area of preventative drug/nutraceutical strategies to delay, halt and stop AD/PD. The findings from the study demonstrate that the aqueous extract of Mu Bie Zi, *Momordica cochinchinensis* seed contains inherent NGF mimetic properties, this being the only extract in the 1144 substances evaluated with this unique property. Imaging analysis using immunocytochemistry (ICC) confirmed that NGF and MCS had similar influence on 3-D orientation/expression of 160/200 kD neurofilament, a protein involved with spinal cord recovery. These findings demonstrate a unique property of MCS extract as having neurotrophic capacity similar to NGF, and thus could have potential for therapeutic application in CNS degenerative disease or injury.

Figure 1A:
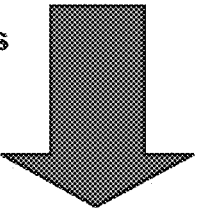
FIG. 1A depicts high throughput screening layout of 1144 plant-based polyphenolics, synthetic/control drugs (including celcoxib, ibuprofen, paclitaxel, etc.) and aqueous extracts of 947 commonly used herbs and spices for ability to induce neurite outgrowth in PC-12 cells relative to a NGF control on collagen coated plates over 7 days. Of the initial screened, with subsequent validation using a full dose range, only one positive NGF mimetic was elucidated.
Figure 1A:
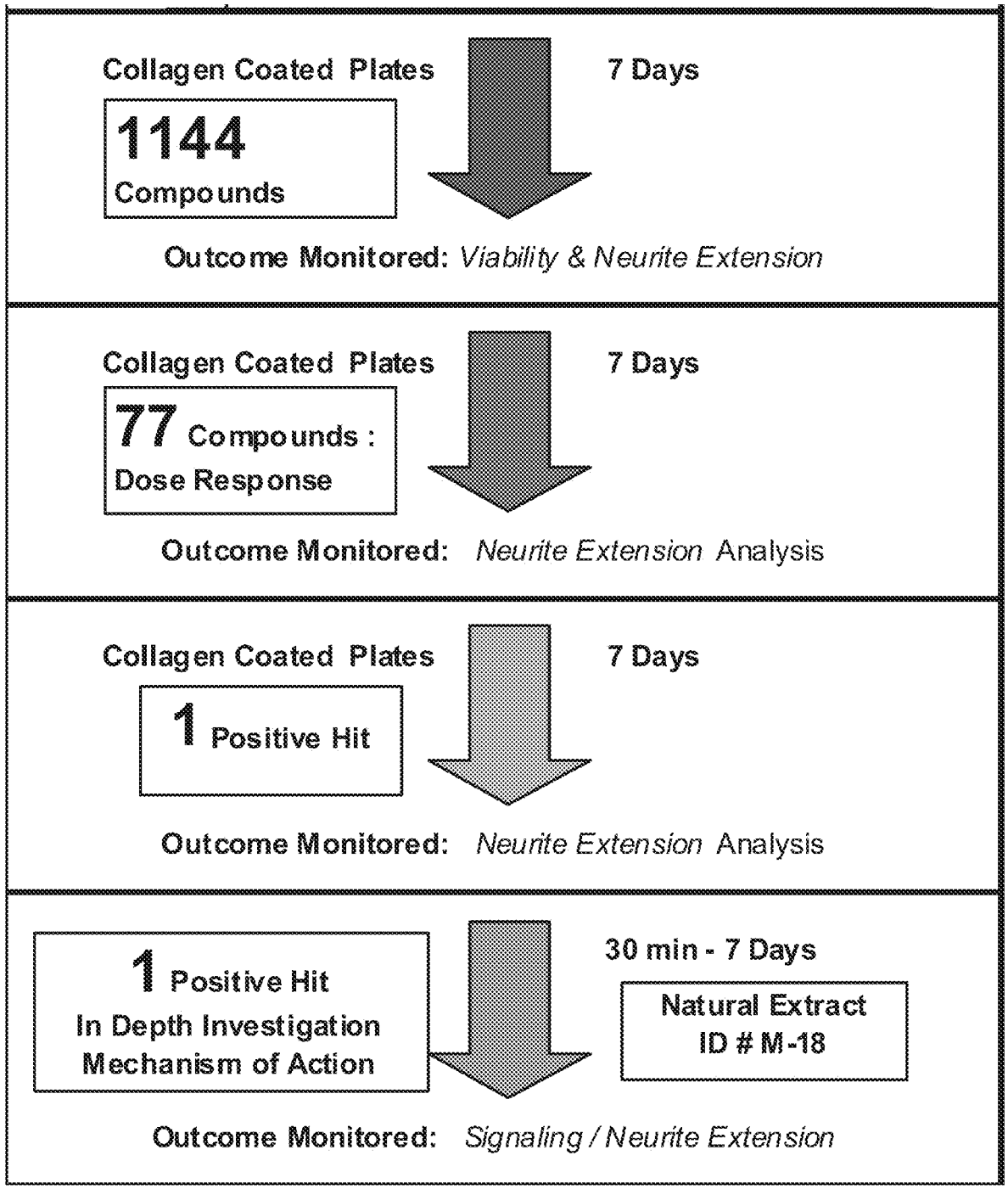

In the current example, an exploratory high-through-put (HTP) screening of 1144 predominantly natural/herb products was conducted for ability to induce neurite outgrowth in a dose dependent manner in PC12 dopaminergic cells grown on rat tail collagen matrix, over 7 days. 29 plant-based polyphenolics (11.12 µg/mL), 168 synthetic/control drugs (including celcoxib, ibuprofen, paclitaxel etc.) (1.112 µg/mL), and extracts of 947 commonly used herbs and spices (111.25 µg/mL) were evaluated for ability to induce neurite extension in PC-12 cells relative to a NGF control on collagen coated plates (FIG. 1A). The data indicate a remarkably rare event—low hit ratio with only 1/1144 tested substances (<111.25 µg/mL) being capable of inducing neurite outgrowth in a dose dependent manner, identified as Mu Bie Zi, *Momordica cochinchinensis* seed extract (MCS).

To quantify the neurotrophic effects of MCS, 36 images (n=6) (average of 340 cells per image) were numerically assessed for neurite length, neurite count/cell and min/max neurite length in microns (µm) using Image J software. The data show neurite elongation from 0.07±0.02 µm (controls) to 5.5±0.62 µm (NGF 0.5 µg/mL) and 3.39±0.45 µm (138 µg/mL) in MCS, where the average maximum length per group extended from 3.58±0.42 µm (controls) to 41.93±3.14 µm (NGF) and 40.20±2.72 µm (MCS). Imaging analysis using immunocytochemistry (ICC) confirmed that NGF and MCS had similar influence on 3-D orientation/expression of 160/200 kD neurofilament, tubulin and F-actin. 36 images were captured also to establish quantitative neurite outgrowth by MCS vs. NGF. Quantification parameters included total cell count/frame; total neurite count/frame; total neurite length/frame; average neurite length/frame; neurite count/cell; neurite length/cell and min and max neurite length. Groups were classified as MCS extract treated (4-138 µg/mL), negative control (-NGF) and positive control (NGF 0.5 µg/mL) (Table 1).

| | | | Image Analysis - MCS vs NGF | | | |
|---|---|---|---|---|---|---|
| | [−] Control | [+] Control Nerve Growth | Mu Bie Zi, *Momordica cochinchinensis* seed | | | |
| | No Treatment | Factor-7S 0.5 µg/mL | 4 µg/mL | 34 µg/mL | 69 µg/mL | 138 µg/mL |
| Total Cell Count/Frame | 412.75 ± 70.72 | 208.78 ± 9.53 | 530.00 ± 71.18 | 342.00 ± 66.89 | 223.29 ± 10.95 | 199.86 ± 15.28 |
| Total Neurite Count/Frame | 11.38 ± 2.52 | 81.00 ± 7.19 | 8.83 ± 1.83 | 23.60 ± 8.79 | 38.71 ± 3.07 | 49.86 ± 6.85 |
| Total Neurite Length (µm)/Frame | 26.08 ± 5.29 | 1117.67 ± 107.47 | 36.45 ± 9.85 | 244.68 ± 88.56 | 408.13 ± 37.28 | 694.43 ± 129.15 |
| Average Neurite Length (µm)/Frame | 2.20 ± 0.10 | 14.41 ± 0.94 | 4.32 ± 1.20 | 10.77 ± 1.87 | 10.62 ± 0.87 | 12.31 ± 1.17 |
| Neurite Count/Cell | 0.01 ± 0.01 | 0.40 ± 0.04 | 0.02 ± 0.01 | 0.08 ± 0.03 | 0.18 ± 0.02 | 0.25 ± 0.04 |
| Neurite Length (µm)/Cell | 0.07 ± 0.02 | 5.52 ± 0.62 | 0.09 ± 0.03 | 0.79 ± 0.31 | 1.86 ± 0.19 | 3.39 ± 0.45 |
| Min Neurite Length (µm) | 1.29 ± 0.12 | 3.14 ± 0.43 | 1.42 ± 0.23 | 2.76 ± 0.55 | 1.98 ± 0.19 | 2.72 ± 0.21 |
| Max Neurite Length (µm) | 3.58 ± 0.42 | 41.93 ± 3.11 | 7.77 ± 0.32 | 27.79 ± 1.09 | 38.26 ± 4.57 | 40.20 ± 3.21 |

Table 1. Statistical and numerical data on neurite outgrowth parameters by image analysis.

These latent changes were associated with early rise in phosphorylated extracellular signal-regulated kinase (ERK) p-Erk1 (T202/Y204)/p-Erk2 (T185/Y187) at 60 min with slight early elevation of pAKT peaking at 5 min, and no indication of pMEK involvement. These findings demonstrate a remarkable infrequency of natural products or polyphenolic constituents to exert neurotrophic effects at low concentrations and elucidate a unique property of MCS extract to do so.

I. Methods and Materials

Hank's Balanced Salt Solution (4-(2-hydroxyethyl)-1-piperazineethanesulfonic acid) (HEPES), ethanol, 96 well plates, rat tail collagen, collagen coated plates, general reagents and supplies were all purchased from SIGMA-ALDRICH Co. (St. Louis, Mo., USA) and VWR International (Radnor, Pa., USA). Imaging probes were supplied by LIFE Technologies (Grand Island, N.Y., USA), natural products were provided by FRONTIER Natural Products Co-op (Norway, Iowa, USA), MONTEREY BAY Spice Company (Watsonville, Calif., USA), Mountain Rose Herbs (Eugene, Oreg., USA), MAYWAY Traditional Chinese Herbs (Oakland, Calif., USA), KALYX Natural Marketplace (Camden, N.Y., USA), FUTURECEUTICALS (Momence, Ill., USA), organic fruit vegetable markets, and Florida Food Products Inc. (Eustis, Fla., USA). The Mu Bie Zi, *M. cochinchinensis* seeds were purchased from PLUM FLOWER BANDS and MAYWAY Traditional Chinese Herbs (Oakland, Calif., USA).

i. Cell Culture

PC-12 cells were obtained from ATCC (Manassas, Va., USA). Cells were cultured in high glucose DMEM [4500 mg/L glucose] containing phenol red, 5% FBS, 4 mM L-glutamine and penicillin/streptomycin (100 U/0.1 mg/mL). The cells were maintained at 37° C. in 5% CO2/ atmosphere. Every 2-5 days, the medium was replaced and the cells sub-cultured. For experiments, cells were disbursed into a homogenous solution of singlet cells and plated at a density of approximately $0.1 \times 10^5$ cells/mL on collagen-coated plates.

ii. High-Throughput/Randomized: Double Bind Study

Natural products were extracted in ethanol and polyphenolics/synthetic drugs in DMSO. Subsequent dilutions were prepared in sterile HBSS (pH 7.4) so that working solutions <0.5% solvent at the highest concentrations. All cell culture flasks, dishes and 96 well plates used in this study were pre-collagen coated, or manually coated with rat-tail collagen and sterilized. For initial screening, PC-12 cells were plated in dispersed monolayers in 96 well plates, experimental treatments were added, and neurite differentiation was monitored throughout a 7-day period, with in depth imaging analysis on day 7.

Visual microscopic observation and notation of neurite outgrowth and necrotic/dead cells was established using a grid panel notation method, without knowledge of treatment—by two independent observers, and viability was later confirmed using resazurin (Alamar Blue) indicator dye [Evans S M, Casartelli A, Herreros E, Minnick D T, Day C, George E, Westmoreland C. Development of a high throughput in vitro toxicity screen predictive of high acute in vivo toxic potential. Toxicol In Vitro. 2001; 15:579-584]. A subsequent validation screen was conducted in an identical manner, where 44 noted toxic compounds were subsequently diluted 1/10 and rescreened so that 100 percent viability was confirmed in all samples. Under these conditions, evidence of neurite outgrowth was again evaluated on the seventh day, relative to NGF treated and untreated controls. Subsequently, any potential hit (defined as any observation of neurite spindle shape or neurite outgrowth however minor) was rescreened over a dose range, followed by a final validation on the single and only substance to exert potent NGF mimetic effects: Mu Bie Zi, *M. cochinchinensis* seed extract in a dose dependent fashion.

iii. Cell Viability

Cell viability was determined using resazurin (Alamar Blue) indicator dye [Evans S M, Casartelli A, Herreros E, Minnick D T, Day C, George E, Westmoreland C. Development of a high throughput in vitro toxicity screen predictive of high acute in vivo toxic potential. Toxicol In Vitro. 2001; 15:579-584]. A working solution of resazurin was prepared in sterile PBS [-phenol red] (0.5 mg/mL) and added (15% v/v) to each sample. Samples were returned to the incubator for 6-8 h and reduction of the dye by viable cells (to resorufin, a fluorescent compound) was quantitatively assessed using a microplate fluorometer, Model 7620, version 5.02 (CAMBRIDGE Technologies Inc., Watertown, Mass., USA) with settings at 550 nm/580 nm (excitation/ emission).

iv. Neurite Outgrowth

Neurite outgrowth was measured using NeuronJ—an ImageJ (IJ?1.46r) plugin enabling the tracing and quantification of elongated neurites. Briefly, 36 images were captured using an inverted microscope (25× objective phase contrast lens), n=6. Samples consisted of PC-12 cell (−) controls, NGF treated (+) controls and cells treated with MCS from; 0.0021, 0.004, 0.0086, 0.0173, 0.0347, 0.0694, 0.1388, 0.2777, 0.5555, and 1.111 µg/mL. Cells were manually counted (average=340 cells per image), and neurite length and count per image were quantified. Statistical analysis from numerical data provided information on average neurite length, neurite count/cell and min/max neurite extension length in microns (µm).

v. Immunocytochemistry and Fluorescence Microscopy

Cells were fixed in 4% paraformaldehyde for 15 min, and subsequently permeabilized in 0.25% triton X-100 prepared in phosphate buffered saline (PBS) for 15 min. Briefly, stock solutions containing fluorescent probes were prepared by dissolving 5 mg/l mL ethanol, then subsequently diluted in HBSS and added to cells: final dye concentration-5 µg/mL propidium iodide (PI) and 6.6 µM (phalloidin). Photographic images reflect ALEXA FLUOR® 488 phalloidin/PI nuclear counter stain and tubulin which were acquired using a TUBULINTRACKER™ OREGON GREEN® 488 Taxol, bis-acetate probe (LIFE Technologies Inc.). Cytoskeletal changes were captured using live morphological imaging and immunocytochemistry on fixed permeabilized cells— using primary rabbit anti-rat neurofilament 160/200 and 200 antibodies, conjugated to goat anti-rabbit ALEXA FLUOR® 488. Samples were analyzed photographically using a fluorescent/inverted microscope, CCD camera and data acquisition using TOUPTEK View (TOUPTEK Photonics Co, Zhejiang, People's Republic of China).

vi. NGF Signaling

Signaling was evaluated using sandwich ELISA kits to assay for quantification of Akt (pS473)+total Akt, Erk1 (pT202/pY204)+Erk2 (pT185/pY187)+total Erk1/2 and Mek1 (pS217/221)+total Mek1. Reagents were purchased from ABCAM (Cambridge, Mass., USA) and manufacturers' protocols were adhered to. Briefly, cells were placed in lysate buffer with protease and phosphatase inhibitors and placed on ice for 30 min. Samples were frozen at −80° C., subject to two rapid freeze thaw cycles and centrifuged. In brief, cells were treated with various concentrations of NGF, or MCS for 15 min to 7 days in order to establish approximate time dependent signaling effects. The largest shift occurred in the phosphorylation of ERK around 60 min. Subsequent signaling studies were conducted (n=4) between 0 and 60 min, where media was removed from the wells; cells were lysed and transferred to replicate wells of the ELISA kits. After linking from 2.5 h to overnight at 4° C., wells were washed and incubated with 1° antibody, followed by a wash and a 2° secondary HRP-conjugated anti-body followed by a final wash which preceded a colorimetric reaction initiated by addition of a TMB substrate solution. After 30 min, a stop solution was added and O.D. measured at 450 nm microplate reader (BIOTEK Instruments, Inc., Wincoski, Vt., USA).

vii. Data Analysis

Statistical analysis was performed using GRAPH PAD PRISM (version 3.0; GRAPH PAD Software Inc. San Diego, Calif., USA) with significance of difference between the groups assessed using a one-way ANOVA, followed by Tukey post hoc means comparison test. $IC_{50s}$ were determined by regression analysis using ORIGIN Software (ORIGINLAB, Northampton, Mass., USA).

II. Results

Figure 1B:
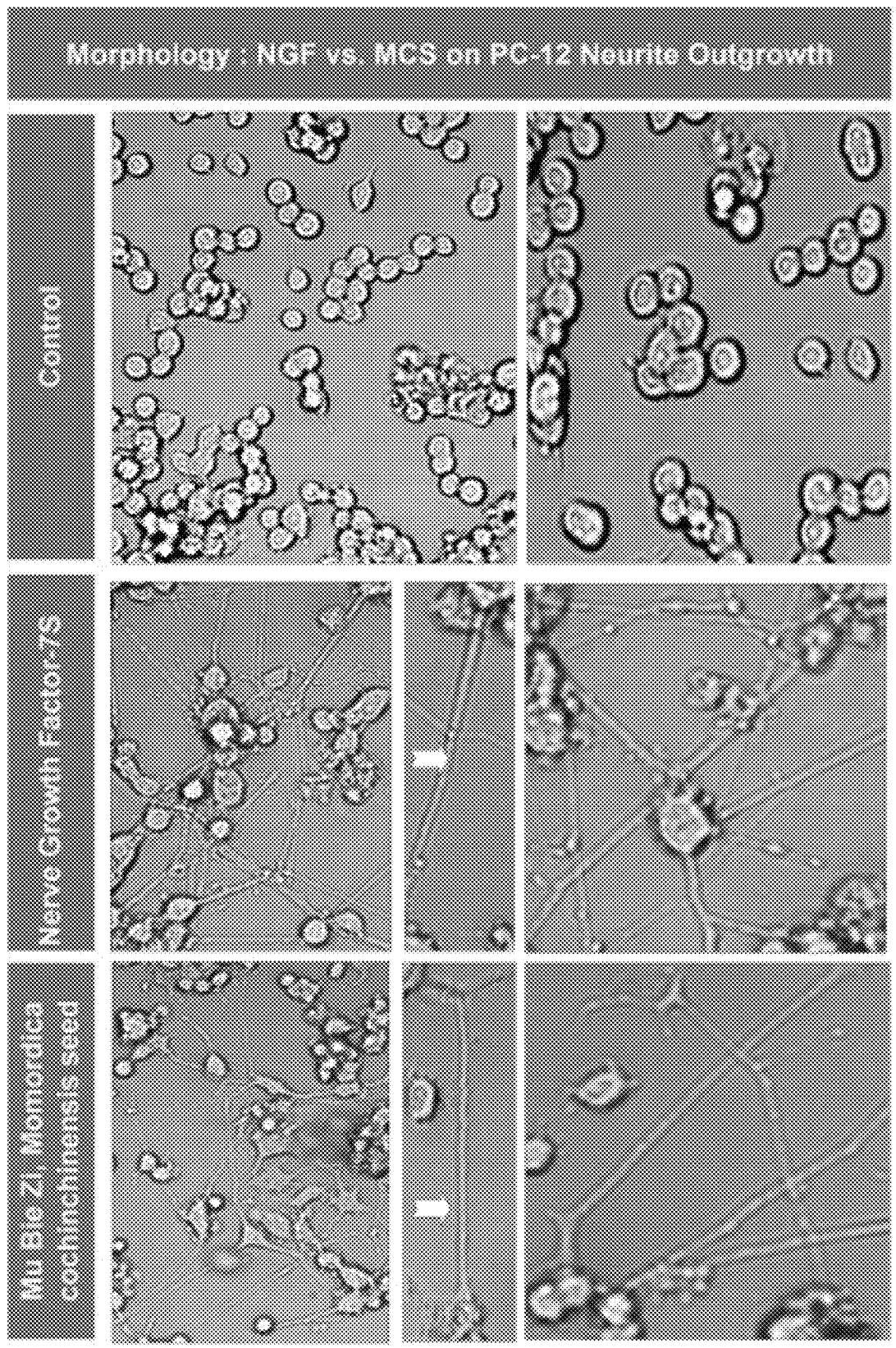
FIG. 1B depicts morphological analysis of neurite outgrowth in PC12 cells at 7 days; controls (top) NGF 0.5 µg/mL (mid) and MCS extract (150 µg/mL) (bottom).

A high through put screening of 1144 compounds: 29 plant based polyphenolics (11.12 µg/mL), 168 synthetic/control drugs (including celcoxib, ibuprofen, paclitaxel etc.) (1.112 µg/mL) and extracts of 947 commonly used herbs and spices (111.25 µg/mL) were evaluated for ability to induce neurite extension in PC-12 cells relative to a NGF control on collagen coated plates (FIG. 1A). The initial screen was conducted twice, using double blind microscopic observations by two individuals. Toxicity was established for 44 compounds, to which the entire screening was repeated, with dilution of these (44) toxic compounds 1:10. A repeat screening for neurotrophic effects of all compounds was conducted, where no toxicity was observed for any experimental treatment [confirmed by Alamar blue (data not shown)]. Lastly, 77 compounds were retested (based on any slight evidence of neurite outgrowth) over a dose response of six concentrations (1-500 µg/mL). Of these, there was one positive hit that caused dose dependent neurite outgrowth. While many of the compounds showed insignificant or meager neurite outgrowth, none of these were dose responsive, except for MCS extract (FIG. 1B), which was identified as a neurotrophin.

Figure 2A:
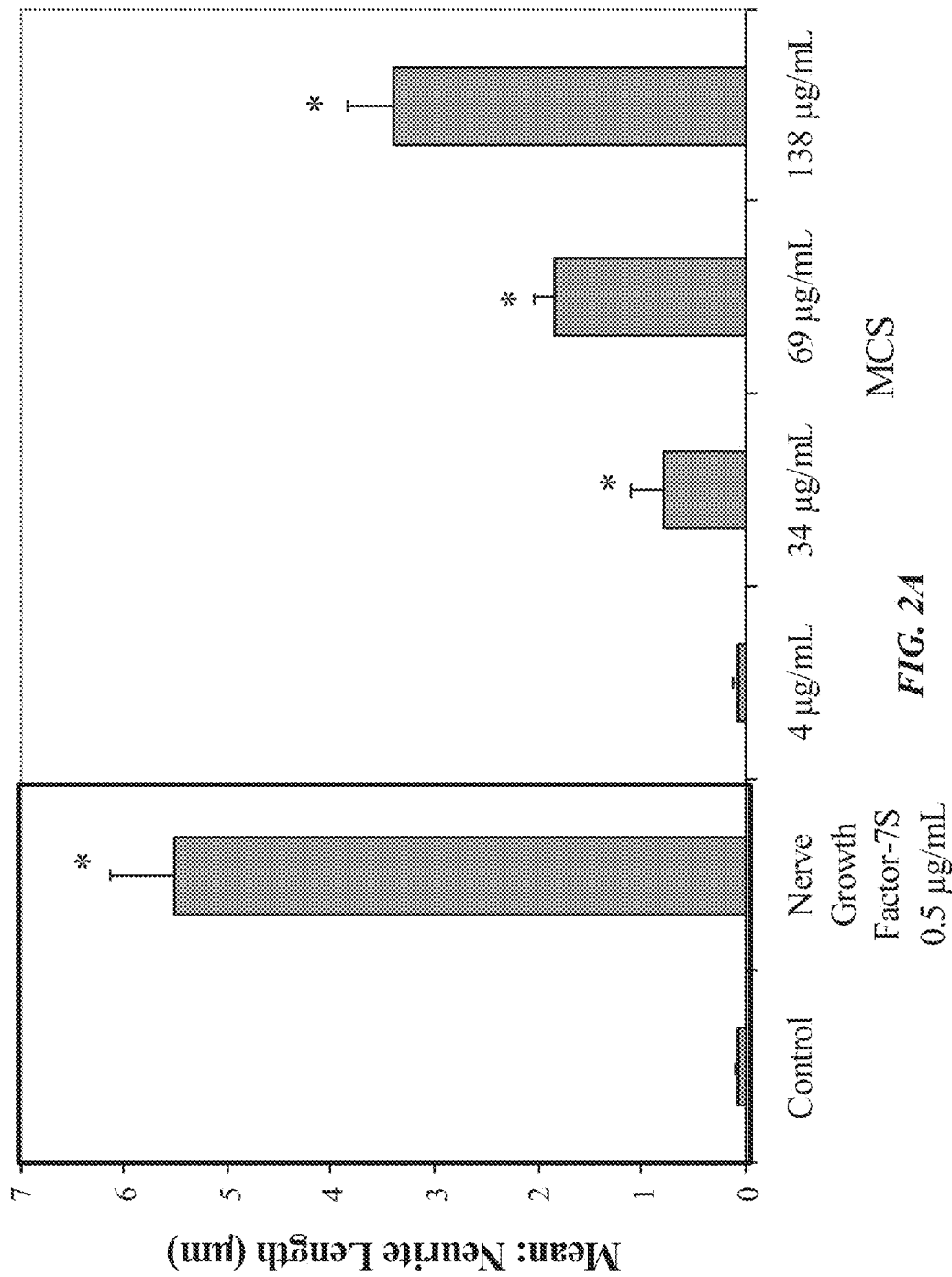
FIG. 2A depicts effects of MCS relative to NGF on neurite extension length in PC12 cells at 7 days. The data represent average neurite length (microns) and are expressed as the mean±SEM, n=6 images. Significant differences from the control were evaluated using a one-way ANOVA, with a Tukey post hoc test, * $P<0.05$.
Figure 2B:
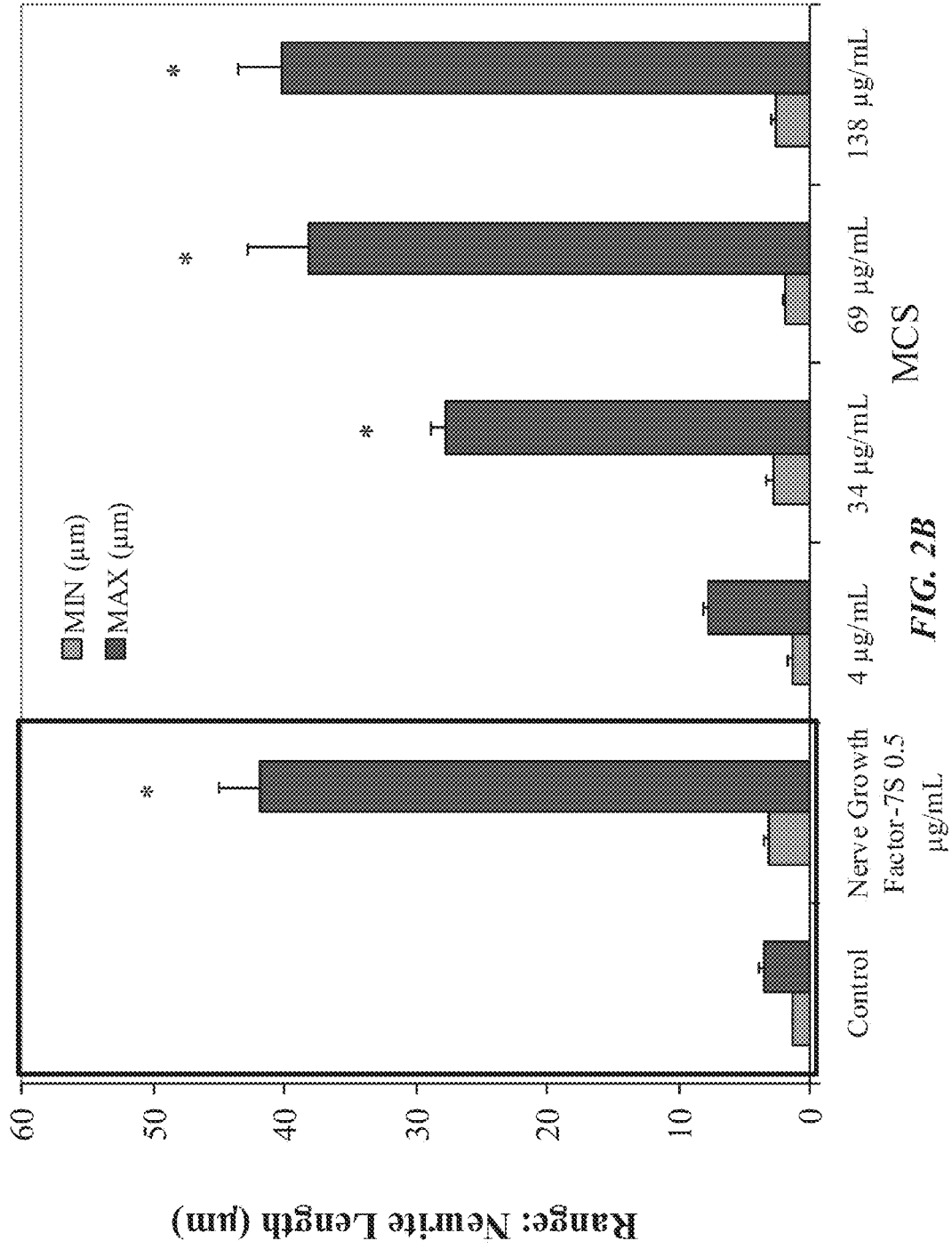
FIG. 2B depicts effects of MCS relative to NGF on neurite minimum and maximum neurite length in PC12 cells at 7 days. The data represent average min or max (microns) and are expressed as the mean±SEM, n=6 images. Significant differences from the control were evaluated using a one-way ANOVA, with a Tukey post hoc test, * $P<0.05$.
Figure 2C:
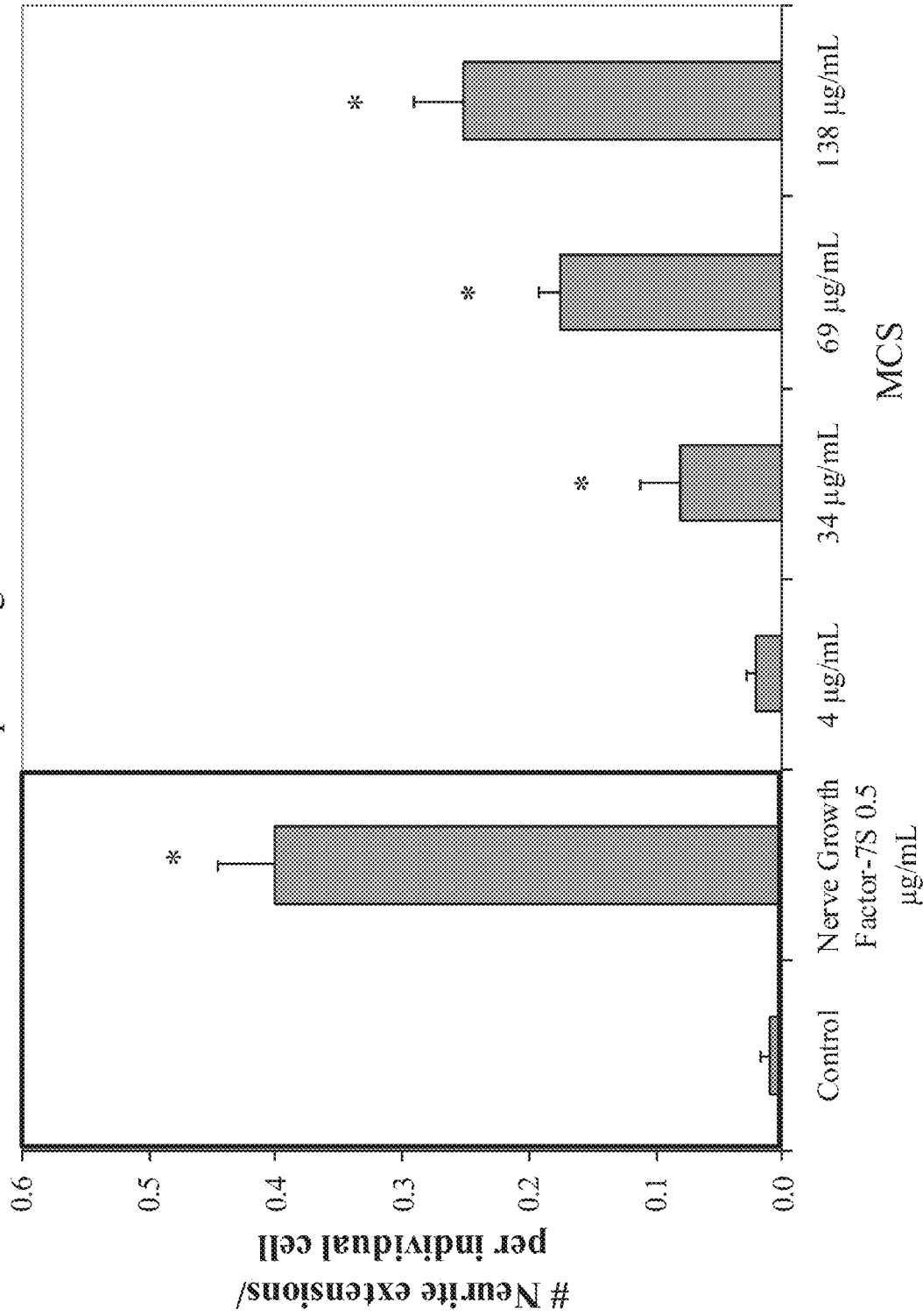
FIG. 2C depicts effects of MCS relative to NGF on neurite outgrowth in PC12 cells at 7 days. The data represent average # neurites/# cells per image, and are expressed as the mean±SEM, n=6 images. Significant differences from the control were evaluated using a one-way ANOVA, with a Tukey post hoc test, * $P<0.05$.

To establish quantitative neurite outgrowth by MCS versus NGF, 36 images were acquired and quantification parameters included total cell count/frame; total neurite count/frame; total neurite length/frame; average neurite length/frame; neurite count/cell; neurite length/cell and min and max neurite length. Groups were classified as MCS extract treated (4-138 µg/mL), negative control (-NGF) and positive control (NGF 0.5 µg/mL) (Table 1). The data show that MCS induced neurite length from an average of 0.07±0.02 microns (control) to 5.5±0.62 microns (NGF 0.5 µg/mL) and 3.39±0.45 microns (138 µg/mL) in MCS (FIG. 2A). Also evident were the changes in maximum neurite length (FIG. 2B), where the average maximum length per group extended from 3.58±0.42 µm (controls) to 41.93±3.14 µm (NGF) and 40.20±2.72 µm (MCS), and neurite extension per cell by NGF and MCS (FIG. 2C). The effects of MCS and NGF were similar in that neurite outgrowth was also associated with cell differentiation, elongated extension and halt of mitosis—corroborated by gradual reduction in cell count per frame.

Figure 3A:
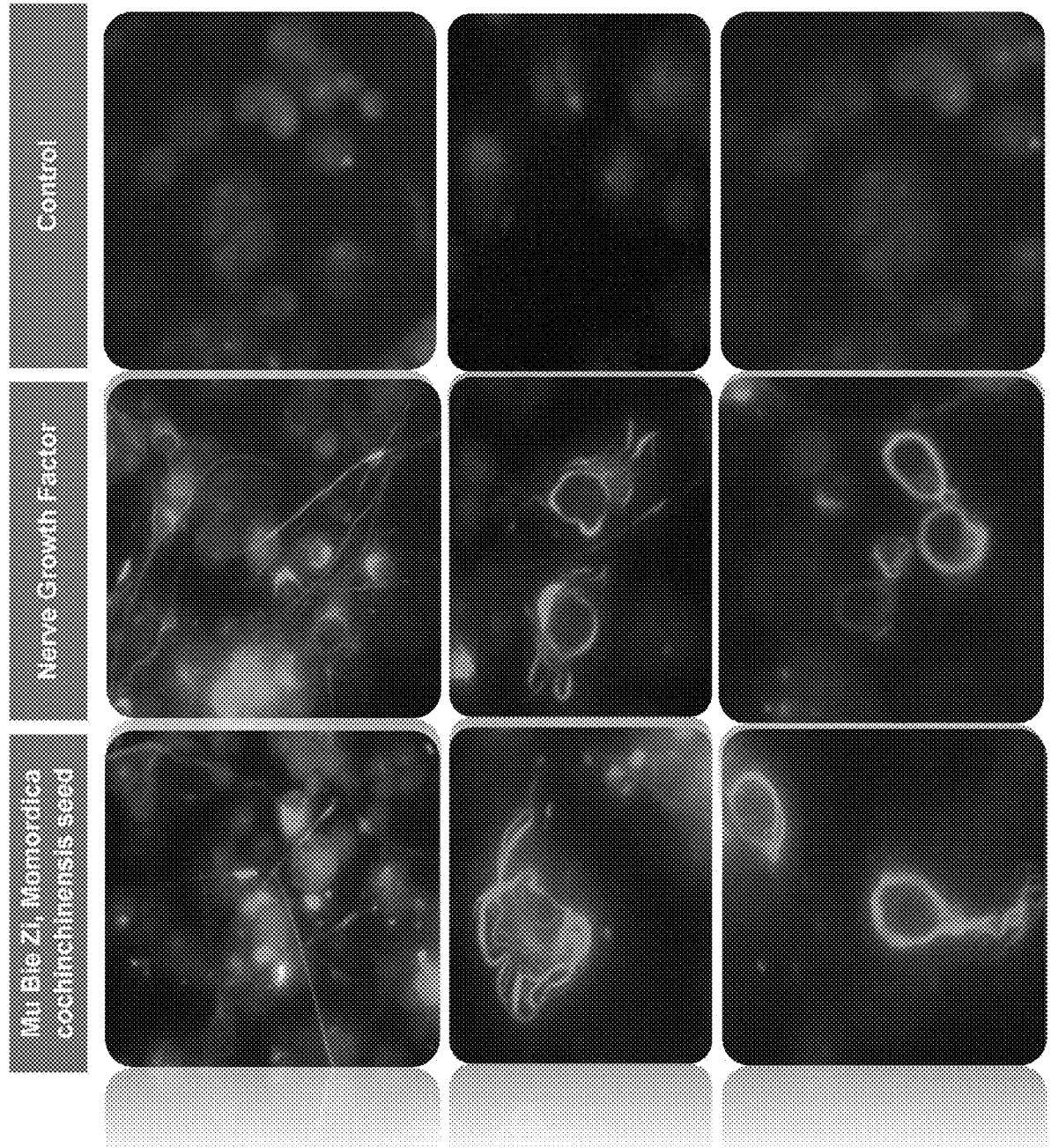
FIG. 3A depicts changes in NF-200 in PC12 cells at 7 days controls; controls (top) NGF 0.5 µg/mL (mid) and MCS extract (150 µg/mL) (bottom).
Figure 3B:
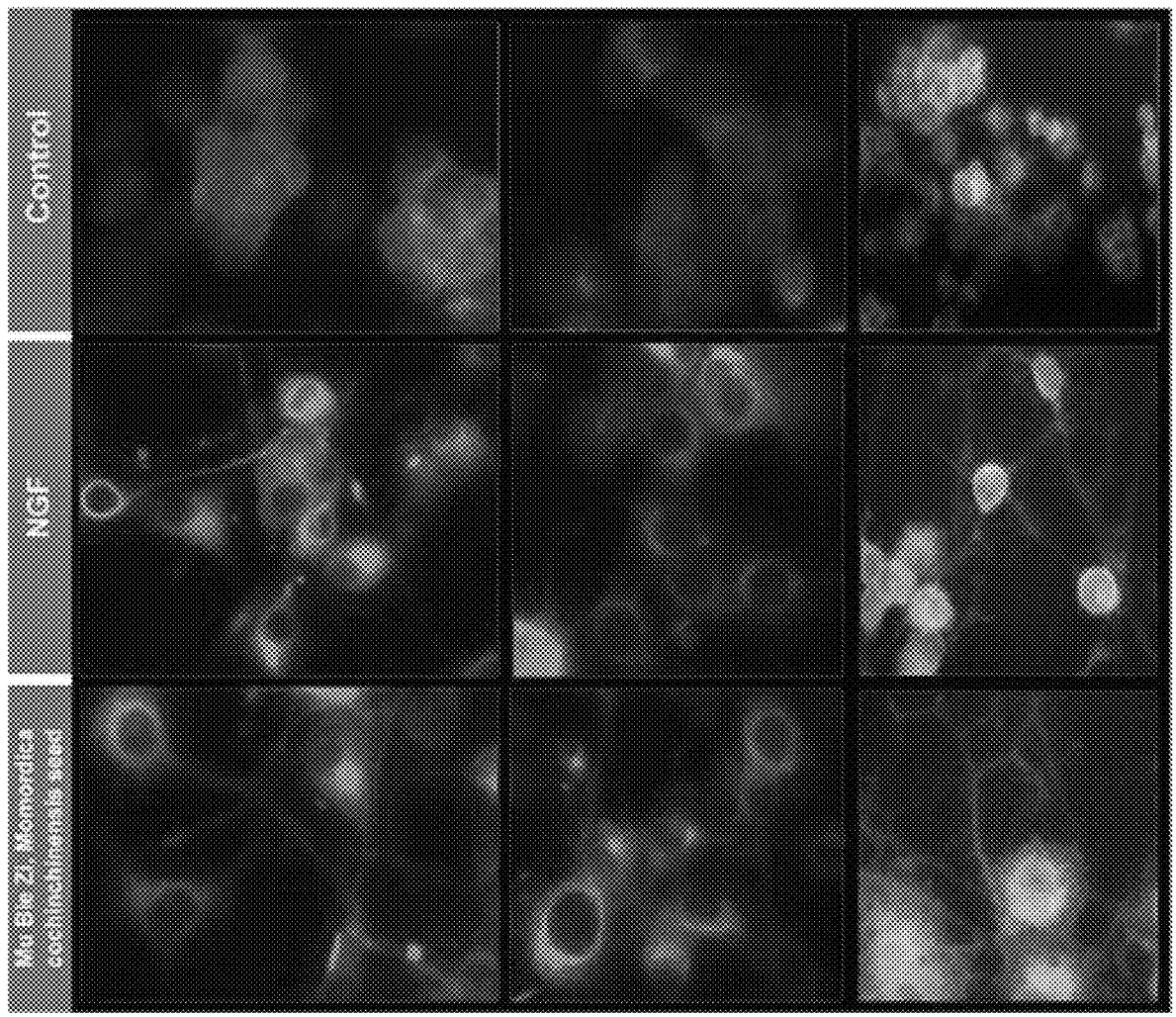
FIG. 3B depicts changes in NF-160/200 kD and Filamentous F-Actin in PC12 cells at 7 days controls; controls (top) NGF 0.5 µg/mL (mid) and MCS extract (150 µg/mL) (bottom).
Figure 3C:
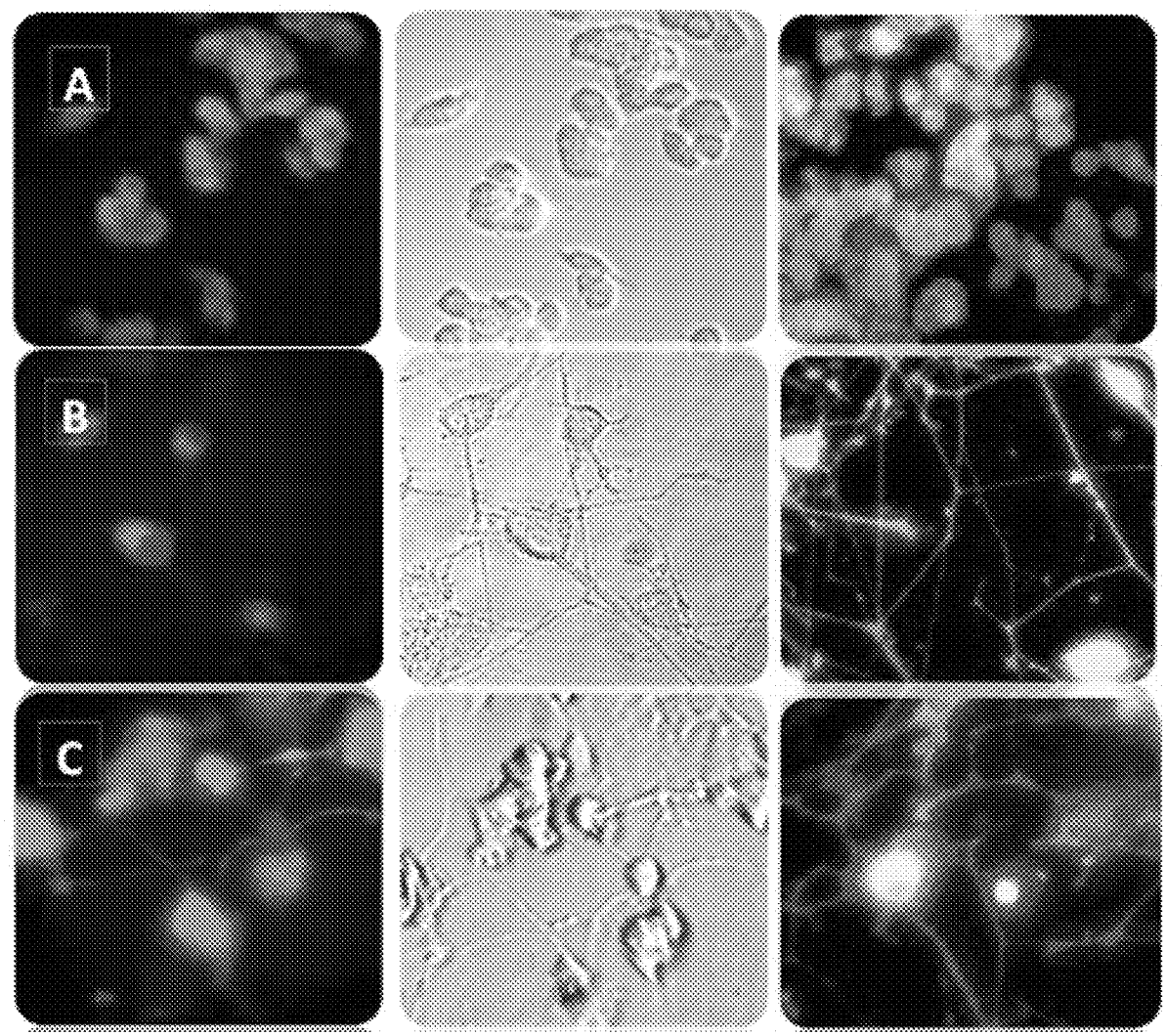
FIG. 3C depicts changes in tubulin (left column), morphology (middle column) and neurite outgrowth (right column) in PC12 cells at 7 days. Row A depicts controls, row B depicts NGF (0.5 µg/mL), and row C depicts MCS extract (150 µg/mL).
Figure 4A:
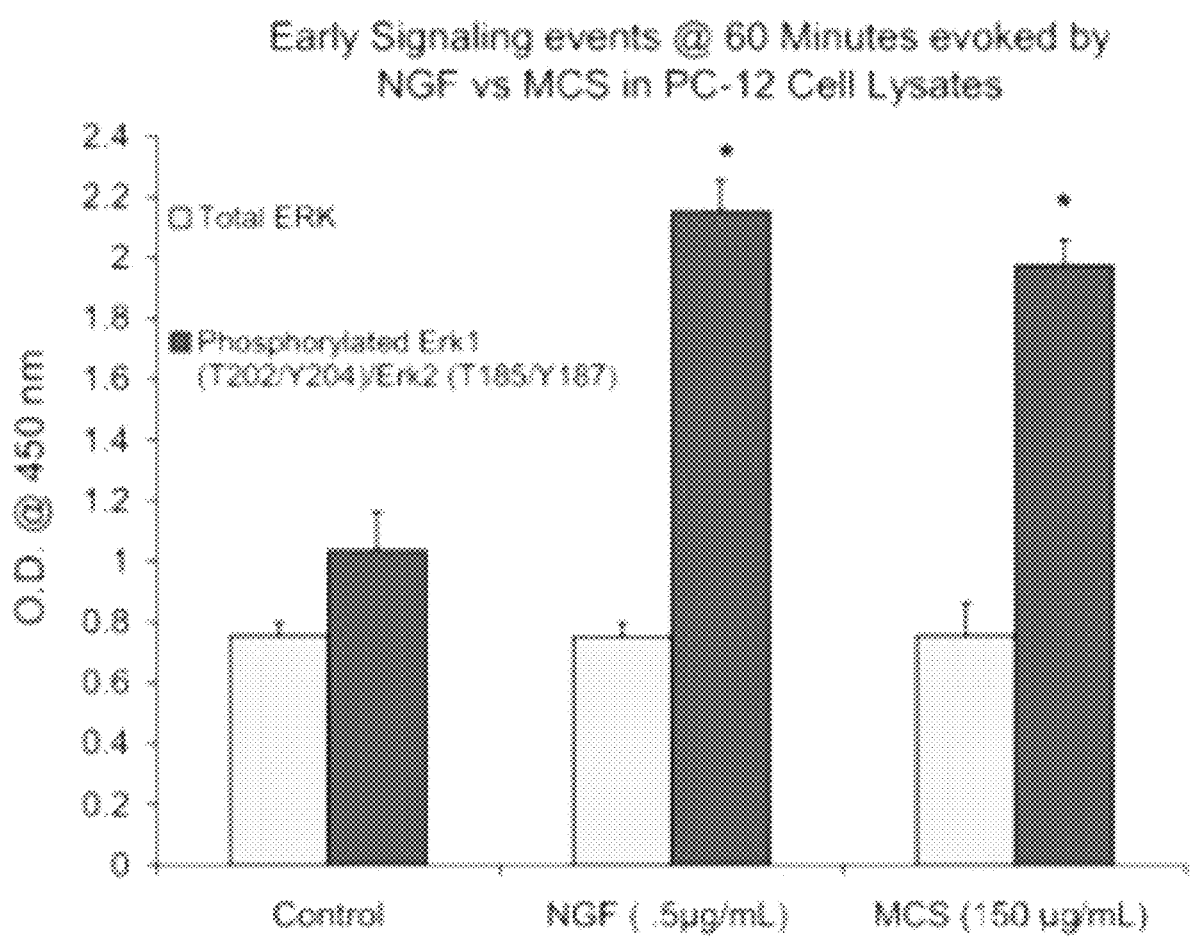
FIG. 4A depicts early pERK1/2 signaling of NGF versus MCS exposure to PC12 cells. The data represent relative Total ERK1/2 and pERK1/2 at 60 min. The data are expressed as the mean±SEM, n=4. Significant differences from the control were evaluated using a one-way ANOVA, with a Tukey post hoc test, *P<0.05.
Figure 4B:
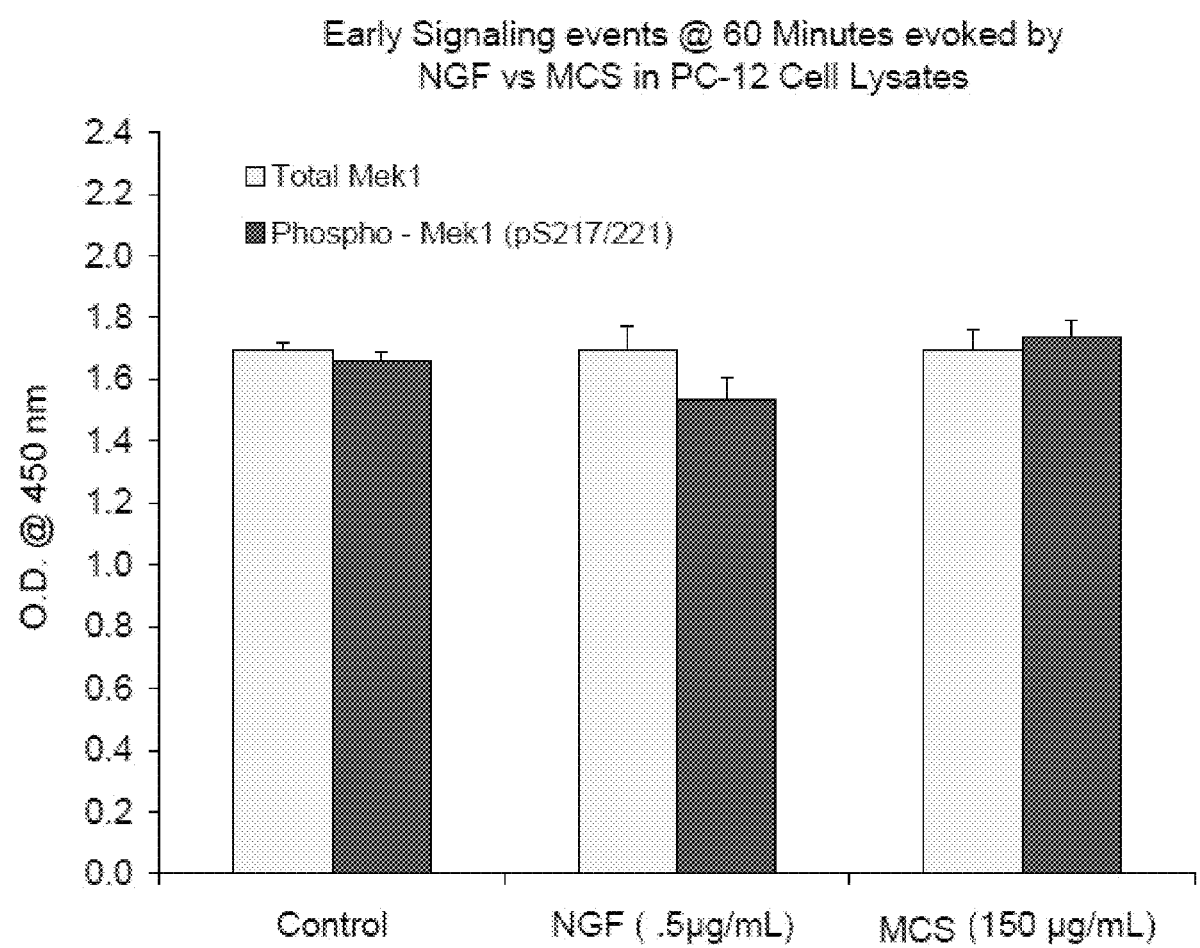
FIG. 4B depicts early MEK signaling of NGF versus MCS exposure to PC12 Cells. The data represent relative Total MEK and pMEK at 60 min. The data are expressed as the mean±SEM, n=4. Significant differences from the control were evaluated using a one-way ANOVA, with a Tukey post hoc test, *P<0.05.
Figure 4C:
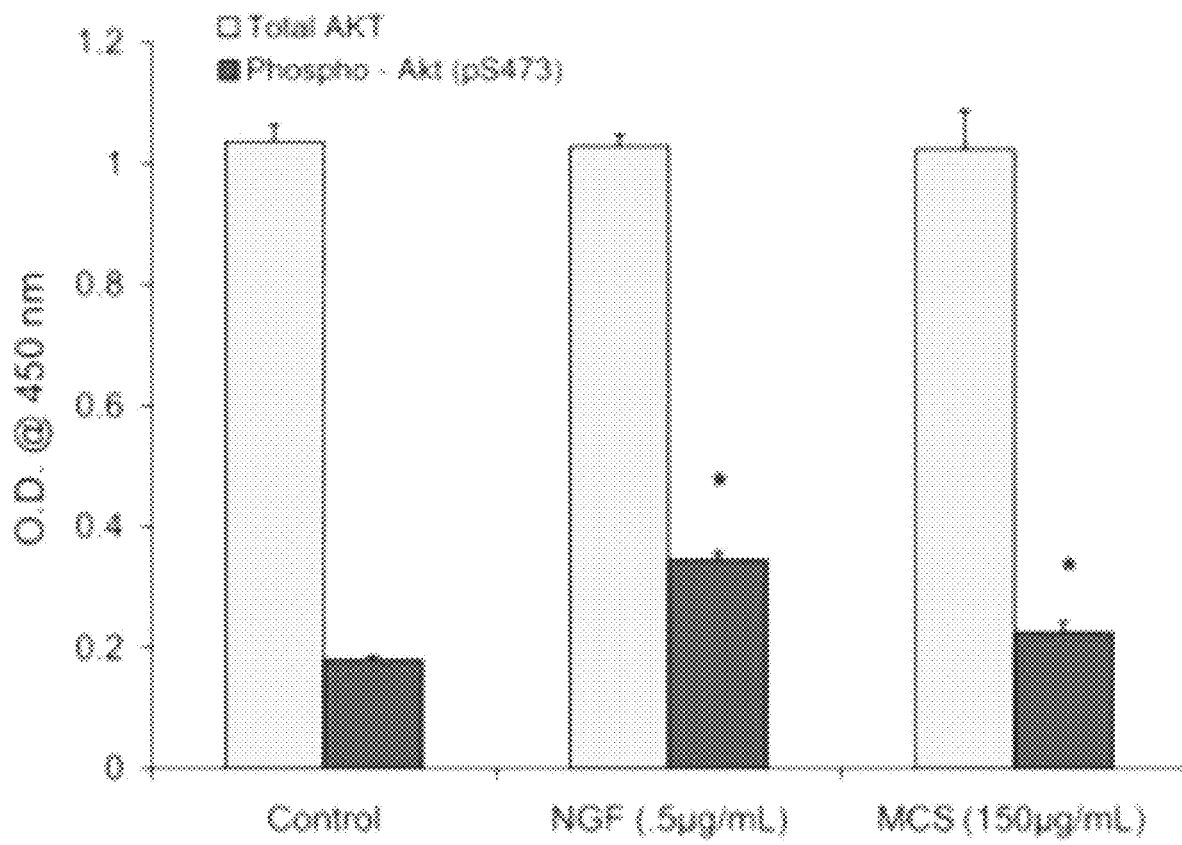
FIG. 4C depicts early AKT signaling of NGF versus MCS exposure to PC12 Cells. The data represent relative Total AKT and pAKT at 5 min. The data are expressed as the mean±SEM, n=4. Significant differences from the control were evaluated using a one-way ANOVA, with a Tukey post hoc test, *P<0.05.

Morphological imaging also showed extensive NGF and MCS neurite development (FIG. 1B), with major changes in structure, organization and concentration of neurofilament of 200 kD (FIG. 3A), F-actin, combined 160/120 kD neurofilaments (FIG. 3B), and tubulin (FIG. 3C). A pilot test evaluating early signaling events associated with NGF and MCS included ERK phosphorylation at 60 min (FIG. 4A), with no effects on MEK/MEK-p (FIG. 4B) and meager phosphorylation of AKT at 5 min after NGF/MCS was added to the cells (FIG. 4C). These findings identify a novel and unique natural compound with NGF mimetic effects, albeit the mechanism of action and constituents within need further elucidation.

Considering the results and data obtained, it can be seen that the capacity of MCS to induce neurite outgrowth in PC-12 cells is less extensive than NGF, but demonstrates a similarity in change of structural proteins such as actin, tubulin and neurofilaments as demonstrated herein. Both NGF and MCS can induce morphological changes NF200, which plays a critical role in preventing axonal neuron degeneration after brain injury [Dileonardi A M, Huh J W, Raghupathi R. Differential effects of FK506 on structural and functional axonal deficits after diffuse brain injury in the immature rat. J Neuropathol Exp Neurol. 2012; 71:959-972] or after spinal cord injury [Cheng L, Liu Y, Zhao H, Zhang W, Guo Y J, Nie L. Lentiviral-mediated transfer of CDNF promotes nerve regeneration and functional recovery after sciatic nerve injury in adult rats. Biochem Biophys Res Commun. 2013; 440:330-335] and used to evaluate efficacy of neurological therapies [Figley S A, Liu Y, Karadimas S K, Satkunendrarajah K, Fettes P, Spratt S K, Lee G, Ando D, Surosky R, Giedlin M, Fehlings M G. Delayed administration of a bio-engineered zinc-finger VEGF-A gene therapy is neuroprotective and attenuates allodynia following traumatic spinal cord injury. PLoS One. 2014; 9:e96137; Chen G, Zhang Z, Wang S, Lv D. Combined treatment with FK506 and nerve growth factor for spinal cord injury in rats. Exp Ther Med. 2013; 6:868-872]. In summary, these findings suggest that the aqueous extract of *M. cochinchinensis* seeds exert NGF mimetic effects through early pERK signaling and morphological changes in structural proteins associated with neurite branching and outgrowth.

Study 2—Protein as the Active Compound

Figure 5:
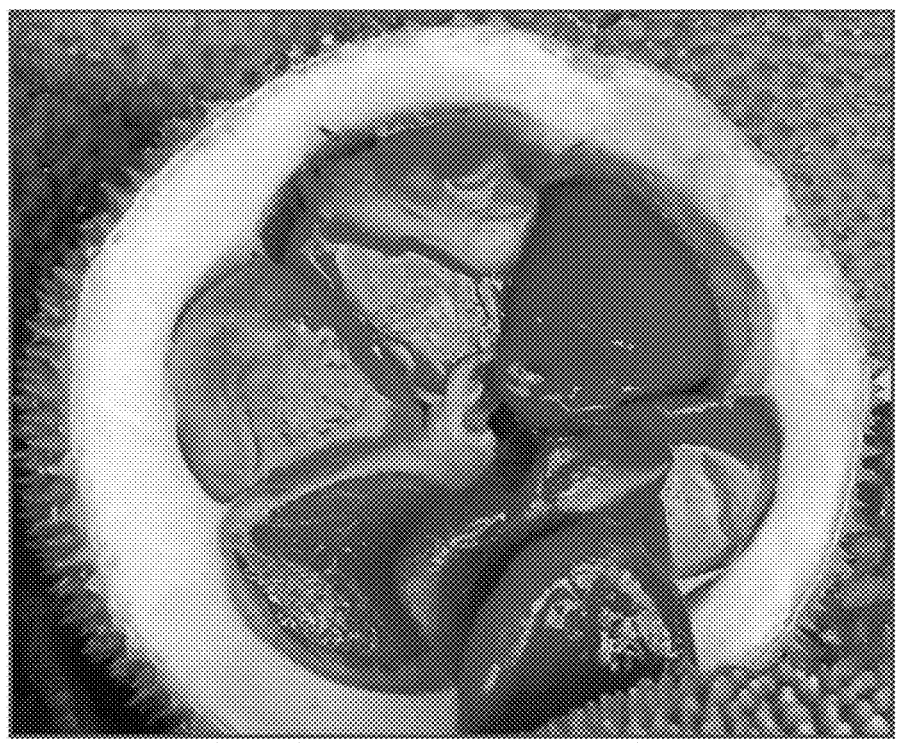
FIG. 5 is an image of *Momordica cochinchinensis* rind (orange), fruit pulp (yellow) and seeds (red aril seed coat).

A high through put screening was completed to determine if any food based nutraceutical has capacity to act as a NGF mimetic. [Mazzio, E., Georges, B., McTier, O., Soliman, K. F., 2015. Neurotrophic Effects of Mu Bie Zi (*Momordica cochinchinensis*) Seed Elucidated by High-Throughput Screening of Natural Products for NGF Mimetic Effects in PC-12 Cells. Neurochemical research 40, 2102-2112] The results from the original screening (Study 1), rendered only one natural product from over 1100 tested, having capacity to act as a NGF mimetic at concentrations less than 200 µg/mL (see Table 1), this one being Mu Bie Zi, *Momordica cochinchinensis* seed pit. These seeds are found within the edible fruit, also known as Gâc fruit or spiny cucumber. The seeds appear highly pigmented due to a peripheral red fleshy pulp (aril) that covers the seeds (see FIG. 5). While the fruit and aril are used in diet, traditional Chinese medicinal reports suggest utility in the seed component for treating boils and rheumatic pain. The current study investigates the constituents contained within the seeds, specifically the constituents that are responsible for the unique NGF mimetic effects in PC-12 cells identified in Study 1.

Generally, crude seed solvent extractions and purified proteins were tested for biological activity and subsequently evaluated for active molecules. The active protein fraction was subject to one-dimensional gel electrophoresis (native), gel staining, sectioning/excision, electro-elution back into solution and re-evaluation for NGF mimetic effects. The mimetic resided in a low abundant visually absent gel section at around 17 kD. The 17 kD gel slice was excised, digested and run on a UPLC-MS/MS—with a Q Exactive Hybrid Quadrupole—Orbitrap Mass Spectrometer. The data were evaluated using X! Tandem, OMS, X Hunter and K-score algorithms. Proteomic evaluation of the 17 kD band confirmed presence of 11S globulin subunit beta, napin, oleosin 18.2 kDa, trypsin inhibitor 1 MCoTI-I/II (known to contain NGF cystine knots) and Two Inhibitor Peptide Topologies TIPTOPs (isoforms 1,2,3,5,6), all with taxonomical identities inherent to the cucumber family (*Momordica cochinchinensis, macrophylla, charantia, Cucumis sativus*). The findings of the study confirm and validate the neurotropic effects of MCS extract and define the active constituent as peptides.

I. Materials and Methods

Hanks Balanced Salt Solution (4-(2-hydroxyethyl)-1-piperazineethanesulfonic acid) (HEPES), ethanol, 96 well plates, rat tail collagen, collagen coated plates, nerve growth factor, general reagents and supplies were all purchased from Sigma-Aldrich Co. (St. Louis, Mo., USA) and VWR International (Radnor, Pa., USA). The Mu Bie Zi, *Momordica cochinchinensis* seeds were purchased from Plum Flower Bands and Mayway Traditional Chinese Herbs (Oakland, Calif.).

i. Cell Culture

PC-12 cells were obtained from ATCC (Manassas, Va.). Cells were cultured in high glucose DMEM [4500 mg/L glucose] containing phenol red, 5% FBS, 4 mM L-glutamine and penicillin/streptomycin (100 U/0.1 mg/mL). The cells were maintained at 37° C. in 5% CO2/atmosphere. Every 2-5 days, the medium was replaced and the cells sub-cultured. For experiments, cells were disbursed into a homogenous solution of singlet cells and plated at a density of approximately $0.1 \times 10^5$ cells/mL on collagen-coated plates.

ii. MCS Seed Extraction

Solvent/Protein Extraction Method 1.

Plant Total Protein Extraction Kit PE0230 (Sigma Aldrich, St. Louis, Mo.) was used and all washes were kept for analysis. 350 mg seeds were homogenized in 1 mL of ethanol, samples were spun down and ethanol was removed. The seed residue was then washed (vortexed 15-30 seconds) 3× with 1 mL of methanol and centrifuged at 16,000×g for 5 minutes at 4° C. Supernatant was collected (Extract 1,2,3) and pellet further extracted. Given the dark green color of the methanol extract, a similar procedure followed with 3× wash with 20 mL of methanol (Extract 4,5,6) to remove all coloring, followed by 2× wash in 1.5 mL of acetone (Extract 7,8). These steps enabled removal of all polyphenolics, tannins, and other chemical substances. The remaining seed residue was dried, weighed and then resuspended in the chaotropic solubilizing protein isolating reagent at 4 µl reagent for each mg seed, then vortexed intermittently for 15 minutes. The sample was centrifuged at 16,000×g for 30 minutes at 4° C., and supernatant (total protein) removed. To exclusion of the final protein isolate, all previous solvent extracts were evaporated and re-dissolved in absolute ethanol and evaluated at 10 concentrations for trophic activity: final working v/v 0.0020%, 0.004%, 0.01%, 0.02%, 0.03%, 0.06%, 0.13%, 0.25%, 0.50%, 1.00% in PC-12 cells grown on collagen coated plates.

Solvent Extraction 2.

Chemical extractions of MCS seeds were carried out using absolute ethanol, ether, hot ethanol, ethanol and ethyl acetate. Solvents were evaporated, reconstituted in ethanol and dilutions prepared in HBSS. The working concentrations were evaluated in PC-12 cells at concentrations of: 0.0020, 0.004, 0.01, 0.02, 0.03, 0.06, 0.13, 0.26, 0.52, 1.04 mg of equal concentration MCS seed/mL. All samples were compared to NGF and crude seed extract at 0.2 mg/mL.

iii. Protein Separation and Electro-Elution

Neurite outgrowth was observed only by the purified seed native protein fraction. Subsequently, both total protein (native) and denatured protein were evaluated, where the latter was prepared using Laemmli sample buffer with 2-mercaptoethanol, boiled for 5 minutes at 100° C. Samples were separated using gradient gels (either 4-20% or 8-16%) Mini-PROTEAN® TGX™ at 200V for 45 minutes. Gels were stained with Blue-band It®, then excised, placed in 20% ethanol in HBSS and electro-eluded back into solution within siliconized micro-centrifuged tubes at 200V, until all bands were back into solution (visible bands—to visible blue solution). Samples were reconstituted in HBSS and evaluated for biological activity on PC-12 cells for any evidence of neurite differentiation relative to NGF-treated (positive) controls and untreated (negative) controls. Subsequently, any potential hit (defined as any observation of neurite spindle shape or neurite outgrowth however minor) was re-sectioned/re-eluted and re-evaluated for NGF mimetic effects in a dose-dependent fashion. All gel sections by process of procedural elimination, left 2 tiny biologically active (non-visual) bands at around 15-17 kD.

iv. Proteomic UPLC-MS/MS Analysis

Biological active gels spots were digested, and sequences identified using an UPLC-MS/MS-using an Q Exactive™ Hybrid Quadrupole-Orbitrap Mass Spec conducted by Bio-proximity LLC (Chantilly, Va., USA). UPLC: Thermo Easy-nLC 1000 Column:C18 reversed phase 50 cm (length) by 75 microns (inner diameter) with integrated nanoelectrospray tip, heated to 50 C Gradient: determined by assay (20 min-4 hours) at 300 nL/minSource: Thermo Easy SprayMS/MS: Thermo Q-Exactive quadrupole-Orbitrap mass spectrometer. Data was searched by up to three tandem mass spectrometry protein identification algorithms, including X!Tandem, OMSSA/K-score, and X!Hunter. Further analysis of each sequence was conducted with a Basic Local Alignment Search Tool (BLAST).

In-Gel Digestion.

Gel bands were cut into 1 mm³ pieces and washed twice with MilliQ water. The gel was de-stained using 1:1 methanol:50 mM ammonium bicarbonate for 1 min, twice. The gel pieces were dehydrated for 5 min using 1:1 acetonitrile:50 mM ammonium bicarbonate followed by acetonitrile for 30 s. The gel pieces were dried in a speed-vac (Thermo Savant) for 10 min. The gel pieces were rehydrated in 5 mM dithiothreitol, 50 mM ammonium bicarbonate and incubated at 56° C. for 20 min. After discarding the supernatant, the gel pieces were incubated in 15 mM iodoacetamide at RT for 20 min in the dark. The gel pieces were washed twice with water and dehydrated and dried as before. The dried gel pieces were rehydrated in 50 mM ammonium bicarbonate containing 250 ng of mass spectrometry-grade trypsin or chymotrypsin (Promega) and incubated overnight at 37 C. Following digestion, the reaction mixture was acidified to 1% tri-flouroacetic acid and desalted.

Peptide Desalting.

The digested peptides were desalted using C18 stop-and-go extraction (STAGE) tips. Briefly, for each sample a C18 STAGE tip was activated with methanol, then conditioned with 60% acetonitrile, 0.5% acetic acid followed by 2% acetonitrile, 0.5% acetic acid. Samples were loaded onto the tips and desalted with 0.5% acetic acid. Peptides were eluted with 60% acetonitrile, 0.5% acetic acid and lyophilized in a SpeedVac (Thermo Savant) to near dryness, approximately 2 h.

Liquid Chromatography-Tandem Mass Spectrometry.

Each digestion mixture was analyzed by UHPLC-MS/MS. LC was performed on an Easy-nLC 1000 UHPLC system (Thermo). Mobile phase A was 97.5% MilliQ water, 2% acetonitrile, 0.5% acetic acid. Mobile phase B was 99.5% acetonitrile, 0.5% acetic acid. The 20 min LC gradient ran from 0% B to 35% B over 10 min, then to 80% B for the remaining 10 min. Samples were loaded directly to the column. The column was 15 cm×75 um I.D. and packed with 2-micron C18 media (Thermo Easy Spray PepMap). The LC was interfaced to a quadrupole-Orbitrap mass spectrometer (Q-Exactive, Thermo Fisher) via nano-electrospray ionization using a source with an integrated column heater (Thermo Easy Spray source). The column was heated to 50 C. An electrospray voltage of 2.2 kV was applied. The mass spectrometer was programmed to acquire, by data-dependent acquisition, tandem mass spectra from the top 20 ions in the full scan from 400-1200 m/z. Dynamic exclusion was set to 15 s, singly-charged ions were excluded, isolation width was set to 1.6 Da, full MS resolution to 70,000 and MS/MS resolution to 17,500. Normalized collision energy was set to 25, automatic gain control to 2e5, max fill MS to 20 ms, max fill MS/MS to 60 ms and the underfill ratio to 0.1%.

Data Processing and Library Searching. Mass spectrometer raw data files were converted to MGF format using msconvert. Detailed search parameters were printed in the search output XML files. Briefly, all searches required 10 ppm precursor mass tolerance, 0.02 Da fragment mass tolerance, strict tryptic cleavage, 0 or 1 missed cleavages, fixed modification of cysteine alkylation, variable modification of methionine oxidation and expectation value scores of 0.01 or lower. MGF files were searched using the specified sequence libraries. MGF files were searched using X! !Tandem using both the native and k-score scoring algorithms and by OMSSA. All searches were performed on Amazon Web Services-based cluster compute instances using the Proteome Cluster interface. XML output files were parsed, and non-redundant protein sets determined using Proteome Cluster. Mass spectrometer RAW data files were also converted to mzXML format using msconvert, processed through several databased using Peaks 8 Studio Peaks 8 Suite (Bioinformatics Solutions Inc. ON Canada).

v. Immunocytochemistry and Fluorescence Microscopy

PC-12 cells were fixed in 4% paraformaldehyde for 15 minutes, and subsequently permeabilized in 0.25% triton X-100 prepared in phosphate buffered saline (PBS) for 15 minutes. Photographic images reflect neurite outgrowth visualized using Molecular Probes® Neurite Outgrowth Staining Kit (Life Technologies Inc.), cytoskeletal changes were captured using live morphological imaging and neurofilament 200 kD was determined using immunocytochemistry in fixed, permeabilized cells, with primary rabbit anti-rat, conjugated to goat anti-rabbit Alexa Fluor® 488 with nuclear counterstain of propidium iodide. Samples were analyzed photographically using a fluorescent/inverted microscope, CCD camera and data acquisition using ToupTek View (ToupTek Photonics Co, Zhejiang, P.R.China).

II. Results

Figure 6:
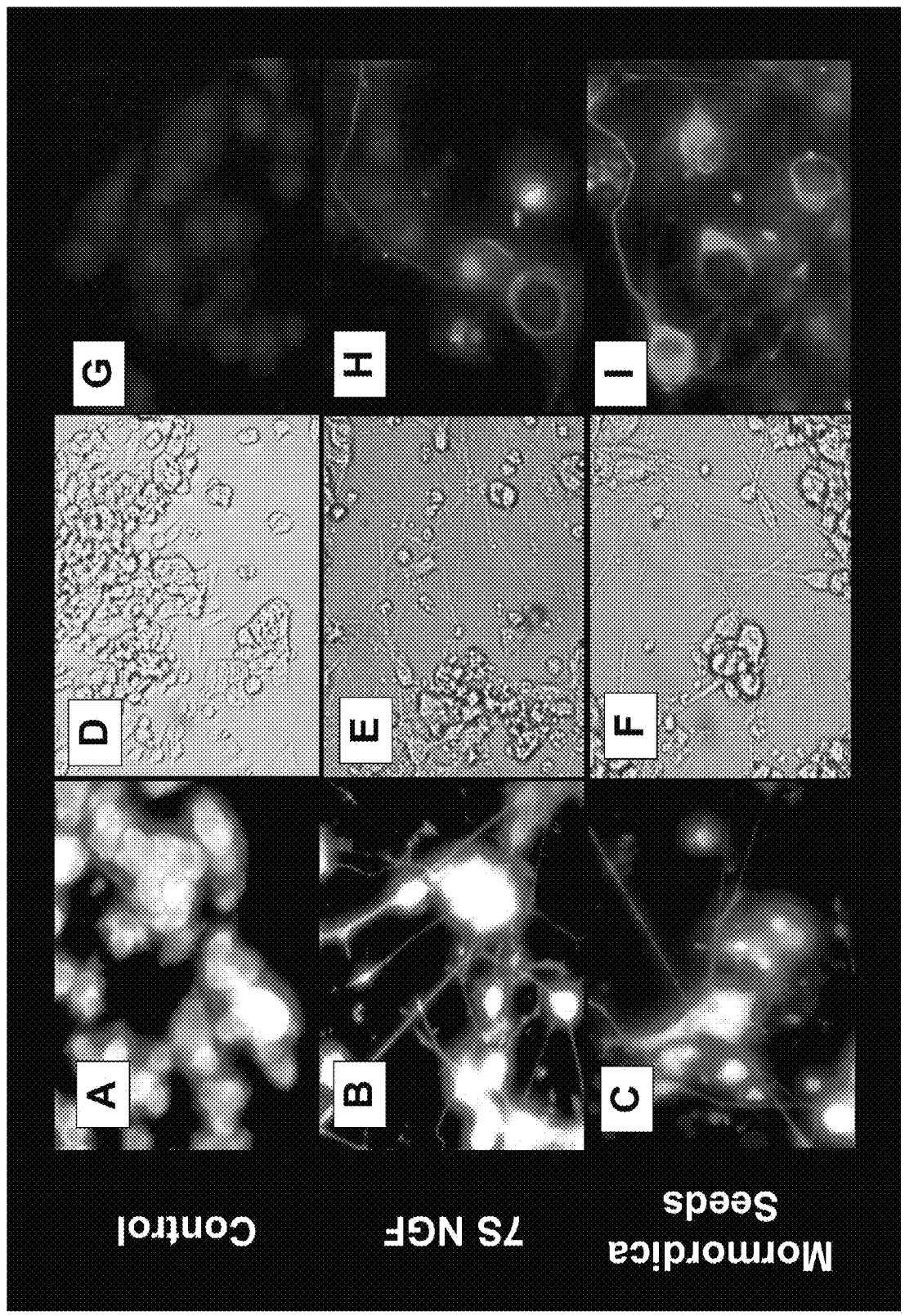
FIG. 6 depicts neurite outgrowth of PC-12 cells at 7 days in collagen coated plates: Controls (top row), NGF 0.5 µg/mL (middle row) and MCS extract (150 µg/mL) (bottom row). Fluorescent imaging (panels A, B, C) demonstrate neurite outgrowth using Molecular Probes® Neurite Outgrowth Staining Kit. Morphology was obtained using phase contrast imaging (panels D, E, F) and changes in neurofilament NF-200 kD was obtained by ICC: primary rabbit anti-rat anti-NF-200 kD, secondary goat anti-rabbit Alexa 488, nuclear counterstained with propidium iodide in fixed permeabilized cells (panels G, H, I) with magnified images of control (panel J) and MCS seed (panel K).
Figure 6:
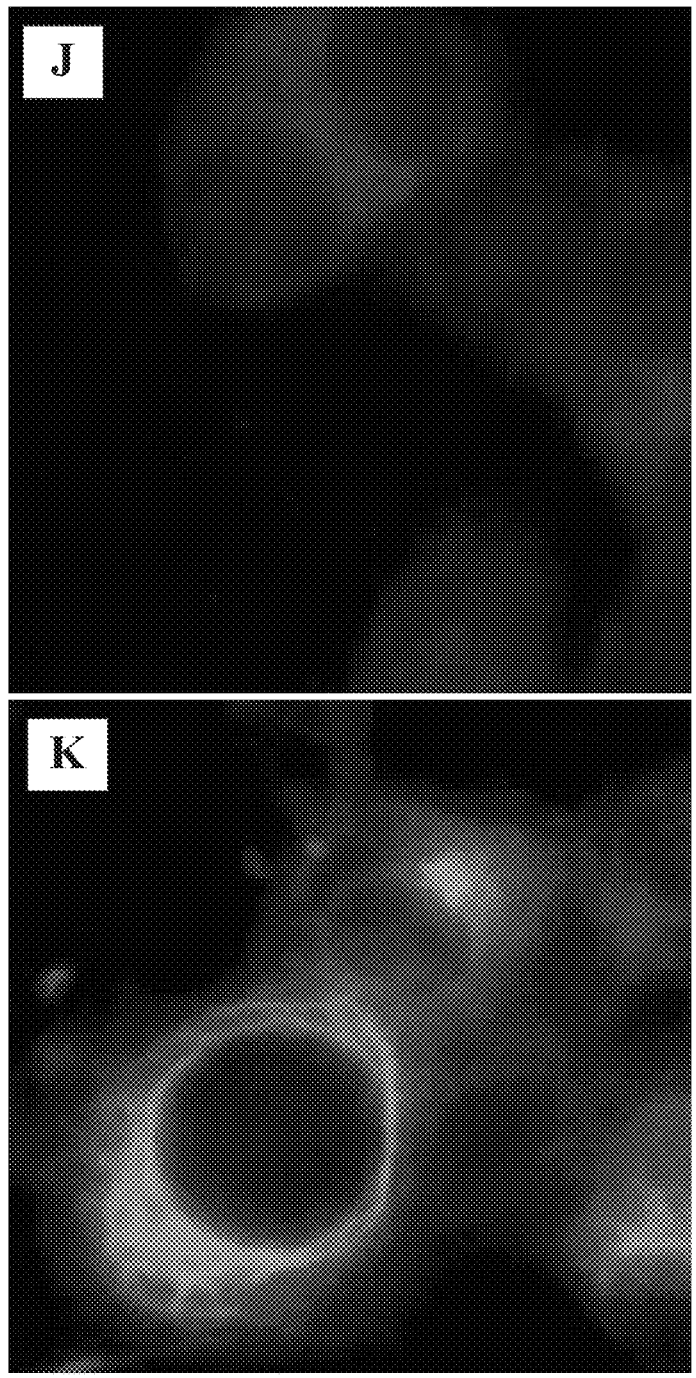

The neurotrophic effects of NGF vs. whole crude unfiltered homogenized ethanol extract of MCS seed (not containing the outer red-aril) was evaluated, with similar findings of those previously reported (Mazzio, E., Georges, B., McTier, O., Soliman, K. F., 2015. Neurotrophic Effects of Mu Bie Zi (*Momordica cochinchinensis*) Seed Elucidated by High-Throughput Screening of Natural Products for NGF Mimetic Effects in PC-12 Cells. Neurochemical research 40, 2102-2112). MCS seed crude extract initiated vast morphological change, neurite outgrowth and dynamic three-dimensional alterations/expression of neurofilament of 160/200 kD in PC-12 cells at a near identical fashion to NGF (see FIG. 6, panels A-I).

Figure 7:
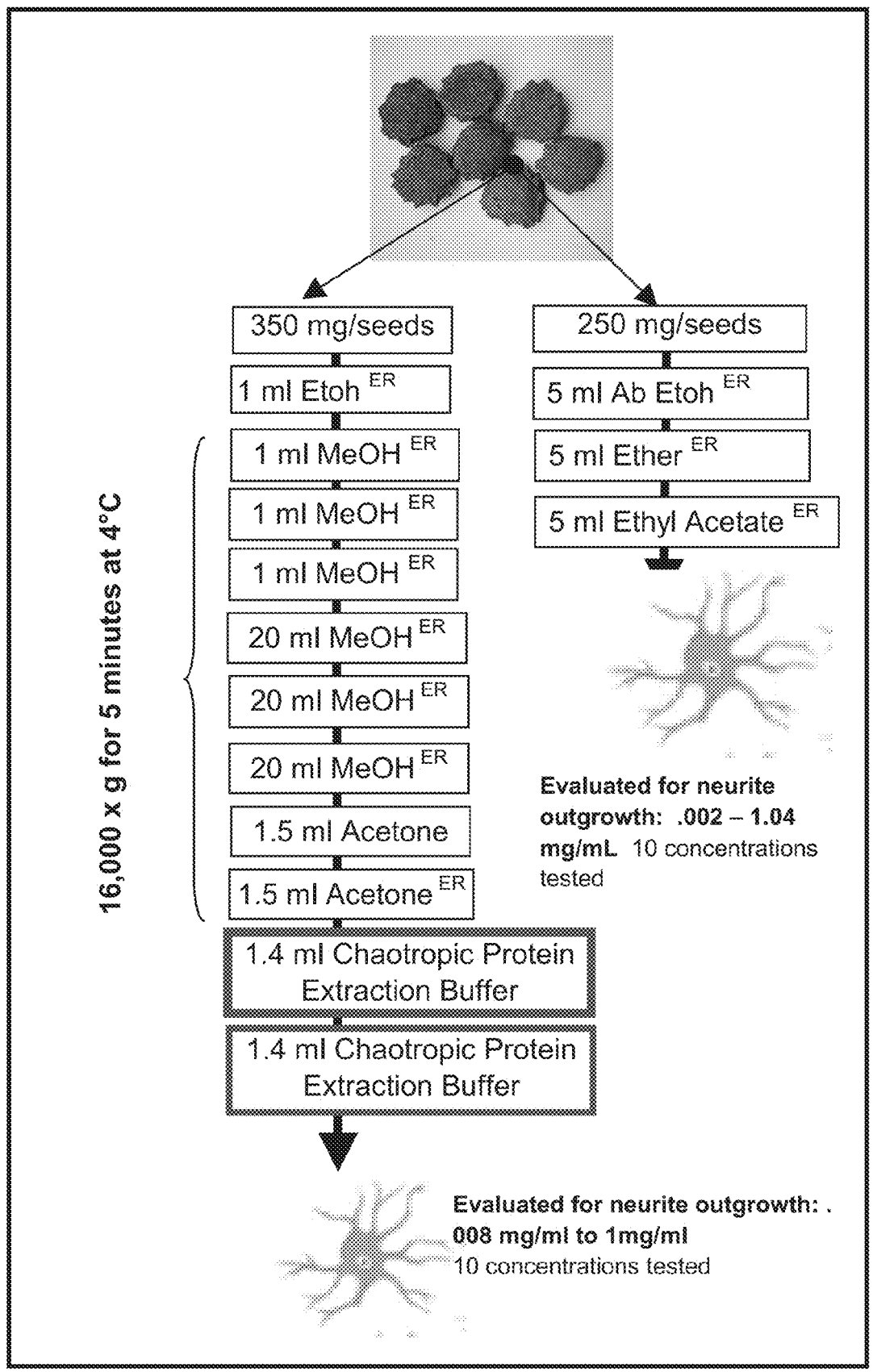
FIG. 7 is a schematic depicting the fractionation schematic solvent/protein extraction method 1 on the left and the solvent extraction method 2 on the right. As it pertains to the fractionation schematic solvent/protein extraction method 1, Plant Total Protein Extraction Kit PE0230 (Sigma Aldrich, St. Louis, Mo.) was used for isolation and all washes were kept for analysis. $^{ER}$ (Evaporated/reconstituted for biological activity testing). Briefly 350 mg seeds were homogenized in 1 mL of ethanol, samples were spun down and ethanol removed. The seed residue was then washed (vortexed 15-30 seconds) 3× with 1 mL of methanol (Extract 1, 2, 3) 3× wash with 20 mL of methanol (Extract 4, 5, 6), followed by 2× wash in 1.5 mL of acetone (Extract 7, 8). Remaining seed residue was suspended in the chaotropic protein centrifuged at 16,000×g for 30 minutes at 4° C., and supernatant (total protein) removed. To exclusion of the final protein isolate, all previous solvent extracts were evaporated and re-dissolved in absolute ethanol and evaluated at 10 concentrations for trophic activity. As it pertains to the extraction method 2, chemical extractions of MCS seeds were carried out using absolute ethanol, ether, hot ethanol, ethanol and ethyl acetate. Solvents were evaporated, reconstituted in ethanol and dilutions prepared in HBSS. The working concentrations were evaluated in PC12 cells at 10 concentrations. All samples were compared to NGF and crude seed extract at 0.2 mg/mL.

To determine the trophic constituents of the seed, a series of chemical extractions were performed. All solvents were evaporated after extraction, then reconstituted (ER) in ethanol 10% and further diluted in HBSS for biological activity evaluation (see the schematic of FIG. 7) Compared to the crude MCS extract (FIG. 8J) and NGF (FIG. 8B), relative to untreated controls (FIG. 8A), solvent fractions failed to induce neurite outgrowth in PC-12 cells, as seen in FIGS. 8C, 8D, 8E, 8G, 8H and 8I. In contrast, total plant protein isolate (FIG. 8F) was effective in enabling neurite outgrowth similar to NGF in a dose-dependent fashion.

Figure 9A:
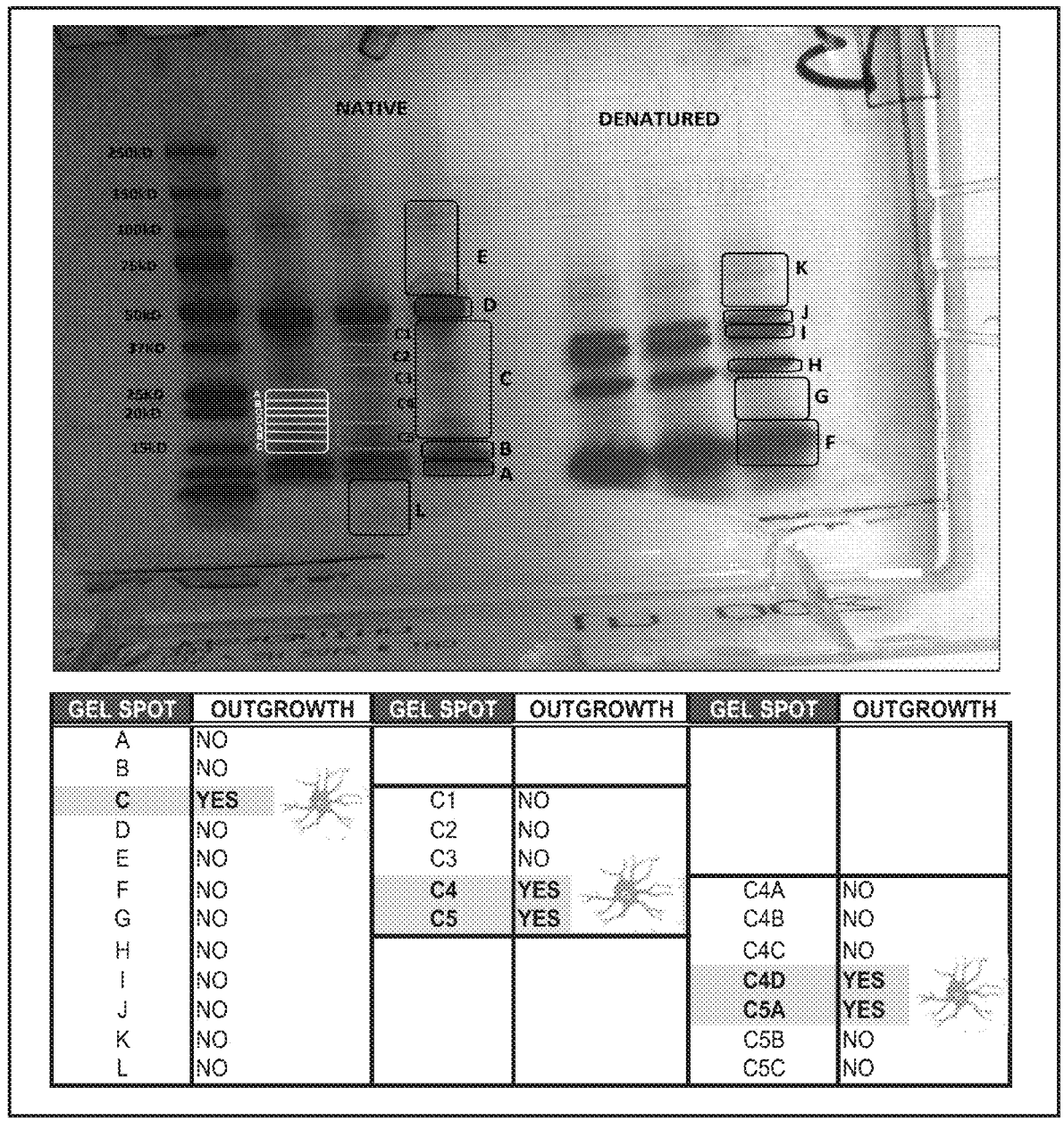
FIG. 9A depicts total seed protein (native) [Left] and denatured [Right] separated using a gradient gel 4-20% Mini-PROTEAN® TGX™ gel at 200V for 45 minutes. Gels were stained with Blue-band It®, washed in ultrapure water then excised, electro-eluded back into solution in siliconized microcentrifuged tubes at 200V. Samples were reconstituted in HBSS and evaluated for biological activity on PC-12 cells for any evidence of neurite differentiation relative to NGF treated (positive) and untreated (negative) controls. All gel sections by process of procedural elimination, left only 2 miniscule biologically active (nonvisual) bands at around 17 kD (C4D) containing the predominant active fraction, with 16 kD C5A to a lesser extent.
Figure 9B:
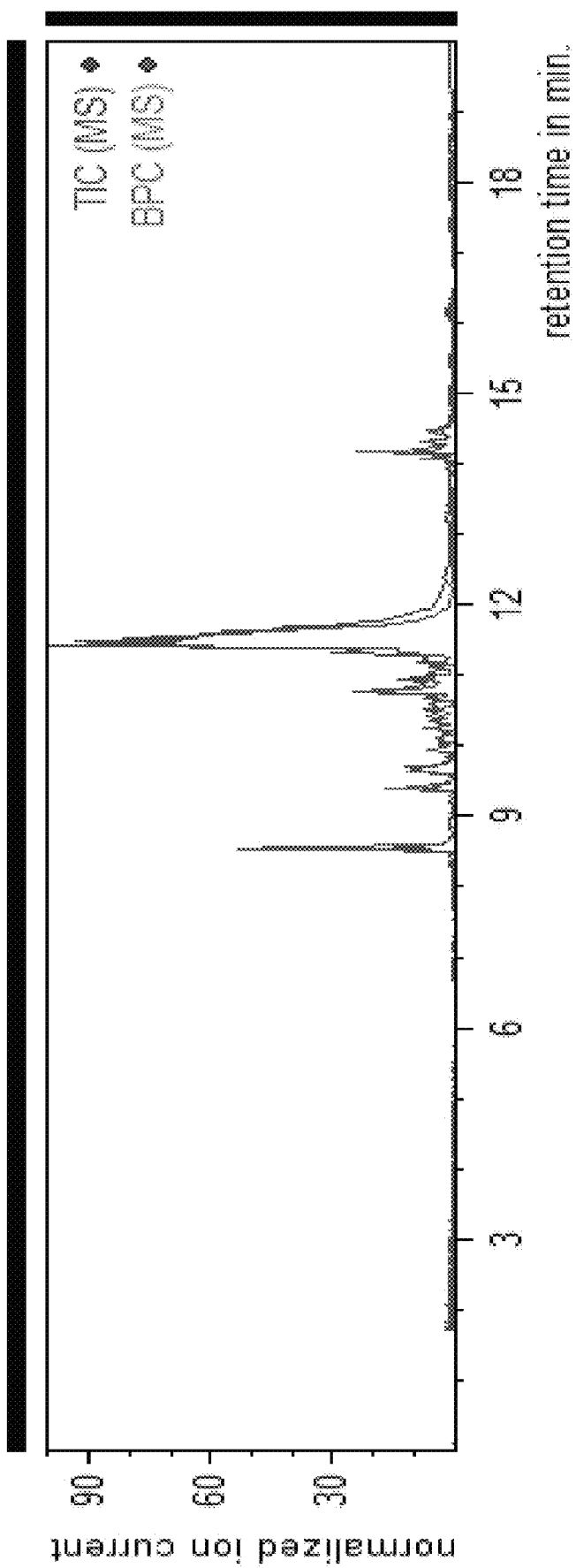
FIG. 9B is a LC-MS Total Ion Chromatogram (TIC) of 17 KD gel slice.
Figure 9C:
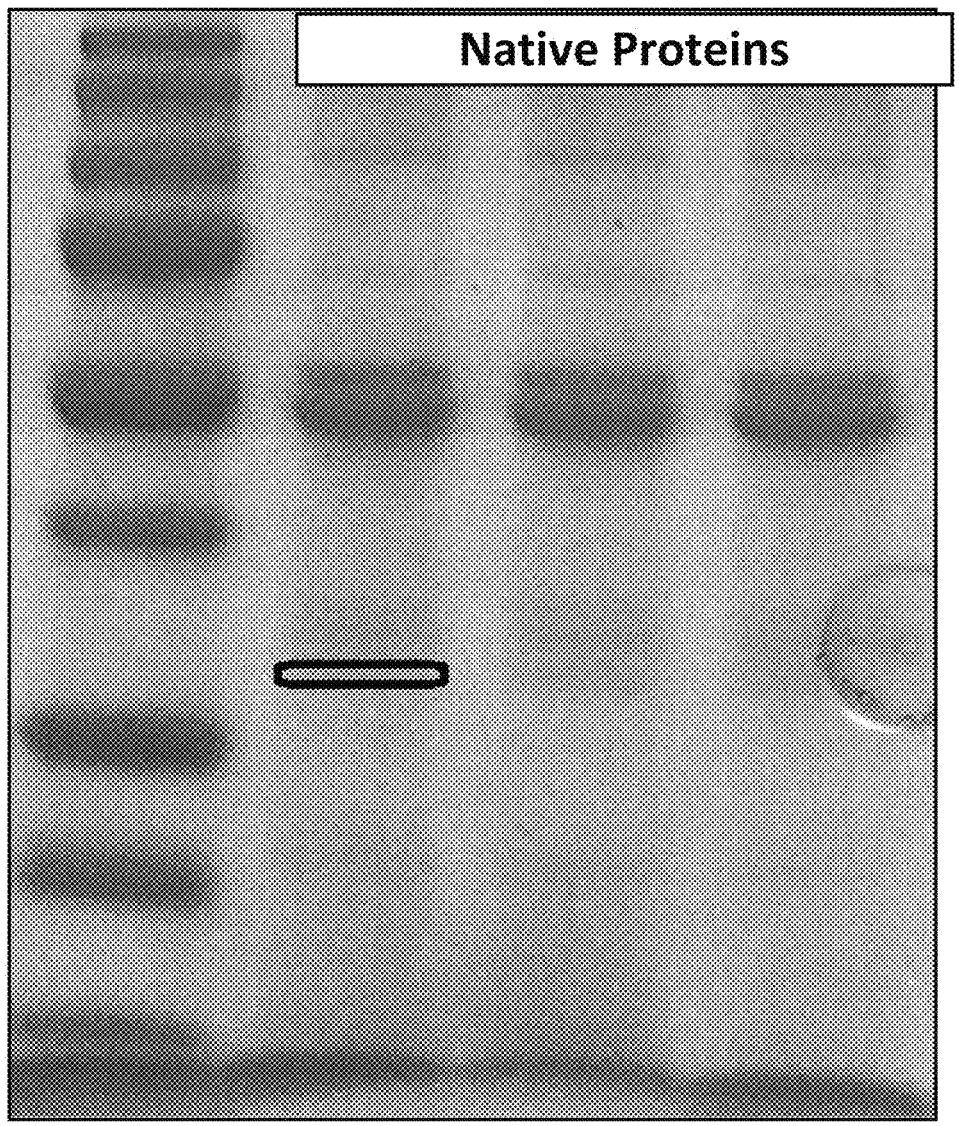
FIG. 9C depicts total seed protein separated using a gradient gel 8-16% Mini-PROTEAN® TGX™ gel at 200V for 45 minutes. Gels were stained with Blue-band It®, washed in ultrapure water then excised, electro-eluded back into solution in siliconized microcentrifuge tubes at 200V. Samples were reconstituted in HBSS and evaluated for biological activity on PC-12 cells. The 17 kD (C4D) band contains the predominant active proteins.
Figure 9D:
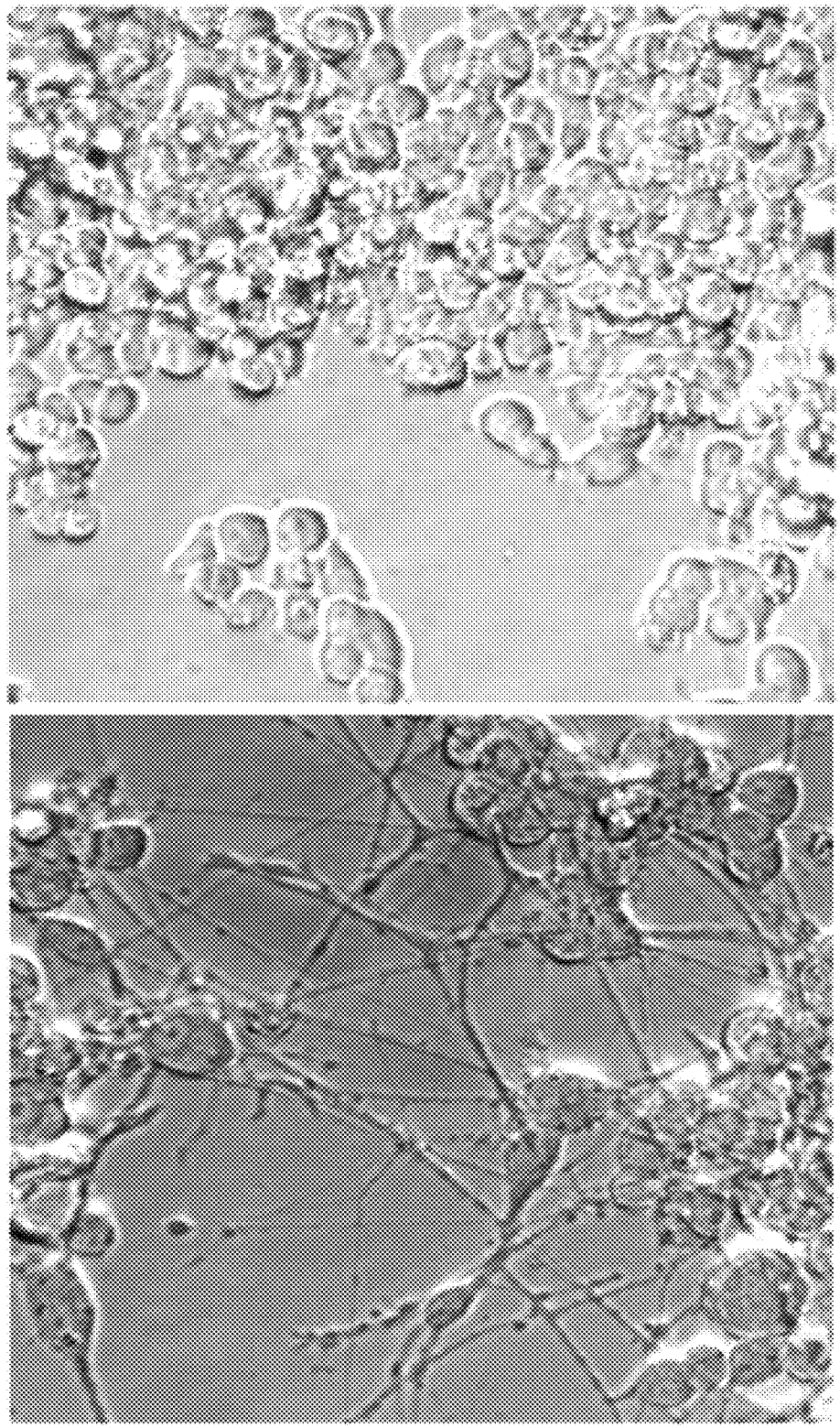
FIG. 9D depicts neurite outgrowth by 17 kD protein electro-elusion in PC-12 cells.

Purified protein was isolated and then separated through a gradient (4-20%) SDS PAGE gel electrophoresis, followed by gel staining, sectioning and electro-elution back into solution for biological activity testing to confirm neurite outgrowth in PC-12 cells (FIG. 9A). All protein gel sections were eliminated as having biological activity, leaving the native protein bands located at approximately 16-17 kD to contain biologic active proteins. The experiment was repeated on 8-16% SDS-PAGE gels, to where the excised gel bands at 17 kD were cut in half. Neurite outgrowth was revalidated and after confirmation, the second tryptic digested half was evaluated by UPLC-MS/MS with a Q Exactive Hybrid Quadrupole-Orbitrap Mass Spectrometer (FIGS. 9B-9D). The data were searched using XTandem, OMSSA and X Hunter. Analysis of each sequence was also conducted using Basic Local Alignment Search Tool (BLAST). Table 2 reflects data represented protein entry ID, description, E-value, Intensity, Peptides found, Identifications, Spectral Counts, Percent Coverage and Species, and genus of protein.

TABLE 2

Biological active gel spots were digested, separated and evaluated by UPLC-MS/MS - using an Q Exactive ™ Hybrid Quadrupole-Orbitrap Mass Spec. Data was searched using several tandem mass spectrometry protein identification algorithms, including X Tandem, OMSSA/K-score. Further analysis of each sequence, was conducted with a Basic Local Alignment Search Tool (BLAST). The data represented protein entry ID, description, E-value, Intensity, Peptides found, Identifications, Spectral Counts, Percent Coverage and Species, and genus of protein.

| Protein | Description | E-value | Intensity | Peptides | IDs | Spectral Counts | Cover-age (%) | Species Genus |
|---|---|---|---|---|---|---|---|---|
| P13744 | 11S globulin subunit beta | −38.9239 | 8.53 | 3 | 17 | 12 | 6.67 | *Cucumis sativus* |
| Q95870 | 7.9 kDa napin-like protein large chain | −33.2037 | 8.84 | 2 | 7 | 6 | 27.27 | *Momordica charantia* |
| A0A0A0LCF7 | Oleosin | −14.6605 | 8.48 | 1 | 8 | 8 | 6.96 | *Cucumis sativus* |
| Q8L694 | Napin | −37.2037 | 8.86 | 3 | 8 | 7 | 17.86 | *Momordica charantia* |
| A0A0A7HIS7 | Two inhibitor peptide topologies 5 | −21.6564 | 8.79 | 2 | 4 | 3 | 12.72 | *Momordica macrophylla* |
| A0A0A7HIA5 | Two inhibitor peptide topologies 6 | −22.3043 | 8.72 | 2 | 5 | 4 | 14.16 | *Momordica macrophylla* |
| P82408 | Trypsin inhibitor 1 MCoTI-I | −22.3043 | 8.72 | 2 | 5 | 4 | 35.29 | *Momordica cochinchinensis* |
| P82409 | Trypsin inhibitor 2 MCoTI-II Chain A, Solution Structure | −22.3043 | 8.72 | 2 | 5 | 4 | 35.29 | *Momordica cochinchinensis* |
| J3RCD6 | Two inhibitor peptide topologies 1 | −22.3043 | 8.72 | 2 | 5 | 4 | 17.08 | *Momordica cochinchinensis* |
| J7IN40 | Two inhibitor peptide topologies 2 | −22.3043 | 8.72 | 2 | 5 | 4 | 17.08 | *Momordica cochinchinensis* |
| J3R9Z5 | Two inhibitor peptide topologies 3 | −27.3498 | 8.72 | 3 | 6 | 4 | 16.71 | *Momordica cochinchinensis* |
| A0A0A0L2N7 | Non-specific serine/threonine protein kinase | −4.21933 | 6.49 | 1 | 1 | 1 | 2.40 | *Cucumis sativus* |
| A0A0A0KNN9 | Elongation factor 1-alpha | −2.284 | 6.70 | 1 | 1 | 1 | 2.74 | *Cucumis sativus* |

The data in this study confirm the efficacy of the purified seed protein fraction as containing the active NGF mimetic component. Total protein was further fractioned and evaluated biologically to where a 15-17 kD low abundant active protein band was isolated. The peptides identified in the gel slice were 11S globulin, napin, oleosin, TIPTOP proteins and *M. cochinchinensis* trypsin inhibitor I (MCoTI-I) and 2 (MCoTI-II). Previous studies have reported these types of unique proteins within the seed pit including low MW cell penetrating dipeptides [Ng, T. B., Chan, W. Y., Yeung, H. W., 1992. Proteins with abortifacient, ribosome inactivating, immunomodulatory, antitumor and anti-AIDS activities from Cucurbitaceae plants. Gen Pharmacol 23, 579-590] such as cochinin B (28 kDa) [Wong, K. L., Wong, R. N., Zhang, L., Liu, W. K., Ng, T. B., Shaw, P. C., Kwok, P. C., Lai, Y. M., Zhang, Z. J., Zhang, Y., Tong, Y., Cheung, H. P., Lu, J., Sze, S. C., 2014. Bioactive proteins and peptides isolated from Chinese medicines with pharmaceutical potential. Chin Med 9, 19] as well as MCoTI-I and MCoTI-II [D'Souza, C., Henriques, S. T., Wang, C. K., Craik, D. J., 2014. Structural parameters modulating the cellular uptake of disulfide-rich cyclic cell-penetrating peptides: MCoTI-II and SFTI-1. Eur J Med Chem 88, 10-18].

The data in this study suggest that the active peptide is MCoTI-II, which belongs to the cyclotide family of plant-derived cyclic peptides that are characterized by a cyclic cystine knot motif [Cascales, L., Henriques, S. T., Kerr, M. C., Huang, Y. H., Sweet, M. J., Daly, N. L., Craik, D. J., 2011. Identification and characterization of a new family of cell-penetrating peptides: cyclic cell-penetrating peptides. J Biol Chem 286, 36932-36943; Chan, L. Y., He, W., Tan, N., Zeng, G., Craik, D. J., Daly, N. L., 2013. A new family of cystine knot peptides from the seeds of *Momordica cochinchinensis*. Peptides 39, 29-35]. MCS derived cyclic knottins share similar conformational form as noncyclic squash inhibitors such NGF [Kliemannel, M., Weininger, U., Balbach, J., Schwarz, E., Rudolph, R., 2006. Examination of the slow unfolding of pro-nerve growth factor argues against a loop threading mechanism for nerve growth factor. Biochemistry 45, 3517-3524]. There is a probability that MCS containing peptides containing a cystine knot similar to that found in NGF is acting directly on the TrkA receptor to initiate signaling.

In conclusion, the findings of this study confirm a very unique protein component of the seed pit of *Momordica cochinchinensis* as beholding a NGF mimetic quality.

Nonlimiting Illustrative Glossary of Claim Terms

About: This term is used herein to refer to approximately or nearly and in the context of a numerical value or range set forth means±15% of the numerical. In an embodiment, the term "about" can include traditional rounding according to significant figures of the numerical value. In addition, the phrase "about 'x' to 'y'" includes "about 'x' to about 'y'".

Administer: This term is used herein to refer to the process by which a composition comprising MCS extract as an active agent, are delivered to a patient or individual for therapeutic purposes. The composition of the subject invention and methodology in use thereof can be administered a number of ways including, but not limited to, parenteral (such term referring to intravenous and intra-arterial as well as other appropriate parenteral routes), subcutaneous, peritoneal, inhalation, vaginal, rectal, nasal, or instillation into body compartments. Administration will often depend upon the amount of compound administered, the number of doses, and duration of treatment. In an embodiment, multiple doses of the agent are administered. The frequency of administration of the agent can vary depending on any of a variety of factors, such as tumor volume/progression, and the like. The duration of administration of the agent, e.g., the period of time over which the agent is administered, can vary, depending on any of a variety of factors, including patient response, etc. The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

Central nervous system disease: This term is used herein to refer to a condition or disorder that affects (i.e., harms, injures) the brain or spinal cord of a patient or subject.

Patient: This term is used herein to refer to humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Pharmaceutically effective carrier: This term is used herein to refer to an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

Reducing or halting progression of neuronal damage associated with a central nervous system disease: This term is used herein to refer to a form of treating the underlying condition or disorder by minimizing or even stopping any additional injury that is being caused to the patient's spinal cord or brain, as compared to injury progression prior to administration of the MCS extract.

Therapeutically effective amount: This term is used herein to refer to concentrations or amounts of components such as agents which are effective for producing an intended result, including neurite outgrowth. Compositions according to the present invention may be used to effect a favorable change in neurite length, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

Total plant protein isolate: This term is used herein to refer to a peptide fraction of the MCS extract.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of inducing neurite outgrowth in vitro in cells in CNS neuronal culture, comprising contacting the cells with a therapeutically effective amount of *Momordica cochinchinensis* seed extract.

2. The method of claim 1, wherein the *Momordica cochinchinensis* seed extract is a total plant protein isolate.

3. The method of claim 2, wherein the total plant protein isolate includes one or more proteins selected from the group consisting of 11S globulin, napin, oleosin, trypsin inhibitor 1 (MCoTI-1), trypsin inhibitor 2 (MCoT-II), and two inhibitor peptide topologies (isoforms 1, 2, 3, 4, 5, 6).

4. The method of claim 2, wherein the total plant protein isolate is further fractionated to a molecular weight of about 15-21 kD.

5. The method of claim 1, wherein the *Momordica cochinchinensis* seed extract includes *Momordica cochinchinensis* trypsin inhibitor II.

6. The method of claim 1, wherein the therapeutically effective amount of *Momordica cochinchinensis* seed extract has a concentration of about 200 µg/mL.

7. The method of claim 1, wherein the therapeutically effective amount of *Momordica cochinchinensis* seed extract has a concentration of about 150 µg/mL.

8. The method of claim 1, wherein the therapeutically effective amount of *Momordica cochinchinensis* seed extract has a concentration of between about 4-138 µg/mL.

* * * * *